(12) United States Patent
Hu et al.

(10) Patent No.: US 6,670,054 B1
(45) Date of Patent: Dec. 30, 2003

(54) ELECTROLUMINESCENT DEVICES

(75) Inventors: Nan-Xing Hu, Oakville (CA); Hany Aziz, Burlington (CA); Zoran D. Popovic, Mississauga (CA); Ah-Mee Hor, Mississauga (CA)

(73) Assignee: Xerox Corporation, Stamford, CT (US)

( * ) Notice: Subject to any disclaimer, the term of this patent is extended or adjusted under 35 U.S.C. 154(b) by 7 days.

(21) Appl. No.: 10/205,632

(22) Filed: Jul. 25, 2002

(51) Int. Cl.[7] .................. H05B 33/14; C07D 209/86
(52) U.S. Cl. .................. 428/690; 428/690; 428/917; 428/704; 548/440; 548/445; 313/504; 313/506; 252/301.16; 252/301.26
(58) Field of Search .................. 548/440, 445; 428/690, 917, 704; 313/504, 506; 252/301.16, 301.26

(56) References Cited

U.S. PATENT DOCUMENTS

| | | | |
|---|---|---|---|
| 4,539,507 A | 9/1985 | VanSlyke et al. | 313/504 |
| 4,720,432 A | 1/1988 | VanSlyke et al. | 428/457 |
| 4,769,292 A | 9/1988 | Tang et al. | 428/690 |
| 5,150,006 A | 9/1992 | VanSlyke et al. | 313/504 |
| 5,151,629 A | 9/1992 | VanSlyke | 313/504 |
| 5,409,783 A | 4/1995 | Tang et al. | 428/690 |
| 5,516,577 A | 5/1996 | Matsuura et al. | 428/212 |
| 5,846,666 A | 12/1998 | Hu et al. | 428/690 |
| 5,942,340 A | 8/1999 | Hu et al. | 428/690 |
| 6,225,467 B1 | 5/2001 | Esteghamatian et al. | 544/180 |
| 6,229,012 B1 | 5/2001 | Hu et al. | 544/180 |

*Primary Examiner*—Deborah Jones
*Assistant Examiner*—Ling Xu
(74) *Attorney, Agent, or Firm*—E. D. Palazzo

(57) ABSTRACT

An electroluminescent device including a first electrode, a second electrode, and situated between the electrodes a carbazole layer of the formula

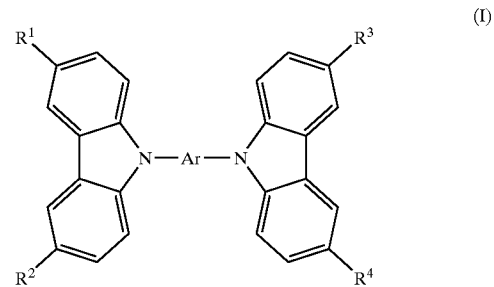

wherein $R^1$, $R^2$, $R^3$, and $R^4$ are independently selected from the group consisting of a hydrocarbyl, and wherein Ar is an aryl.

38 Claims, 2 Drawing Sheets

ELECTROLUMINESCENT DEVICES

RELATED PATENT APPLICATIONS

Illustrated in copending U.S. Pat. No. 6,562,982 B1, the disclosure of which is totally incorporated herein by reference, filed concurrently herewith, is a carbazole

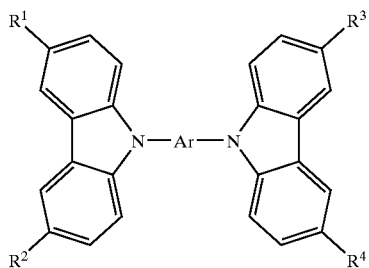
(I)

wherein $R^1$, $R^2$, $R^3$, and $R^4$ are independently a hydrocarbyl, and wherein Ar is an aryl.

Illustrated in copending applications U.S. Ser. No. 09/935,031 on "Oleds Having Light Absorbing Electrode", filed on Aug. 22, 2001; U.S. Ser. No. 10/005,930 on "Organic Devices", filed on Nov. 8, 2001; U.S. Ser. No. 10/005,404 on "Red Organic Light Emitting Devices", filed Nov. 8, 2001; U.S. Ser. No. 10/005,970 on "Organic Light Emitting Devices", filed Nov. 8, 2001; U.S. Ser. No. 10/005,993 on "Organic Light Emitting Devices, filed Nov. 8, 2001; and U.S. Ser. No. 10/005,518 on "Green Organic Light Emitting Devices", filed Nov. 8, 2001, the disclosures of each application being totally incorporated herein by reference, are a number of electroluminescent devices. The appropriate components and process of these copending applications may be selected for the devices of the present invention in embodiments thereof.

BACKGROUND

This invention is related to organic electroluminescent (EL) devices, and more specifically, to organic EL devices with excellent performance characteristics. Organic EL devices are desired that are capable of providing uniform luminescence, saturated color in blue, green and red, and low driving voltages. The organic EL devices of the present invention enable in embodiments the aforementioned characteristics, and which devices contain charge transport/luminescent materials comprised of a new class of carbazole compounds, and wherein these devices can be selected for use in flat-panel emissive display technologies, including TV screens, computer screens, and the like.

REFERENCES

An organic EL device can be comprised of a layer of an organic luminescent material conductively sandwiched between an anode, typically comprised of a transparent conductor, such as indium tin oxide, and a cathode, typically a low work function metal such as magnesium, calcium, aluminum, or the alloys thereof with other metals. The EL device functions on the principle that under an electric field, positive charges (holes) and negative charges (electrons) are respectively injected from the anode and cathode into the luminescent layer and undergo recombination to form excitonic states which subsequently emit light. Several prior art organic EL devices have been constructed from a laminate of an organic luminescent material and electrodes of opposite polarity, which devices include a single crystal material, such as single crystal anthracene. However, these devices usually require excitation voltages on the order of 100 volts or greater.

Organic EL devices with a multilayer structure can be formed as a dual layer structure comprising one organic layer adjacent to the anode supporting hole transport, and another organic layer adjacent to the cathode supporting electron transport and acting as the organic luminescent zone of the device. Another alternate device configuration is comprised of three separate layers, a hole transport layer, a luminescent layer, and an electron transport layer, which layers are laminated in sequence and are sandwiched between an anode and a cathode. Optionally, a fluorescent dopant material can be added to the emission zone or layer whereby the recombination of charges results in the excitation of the fluorescent dopant material.

In U.S. Pat. No. 4,539,507, the disclosure of which is totally incorporated herein by reference, there is disclosed an EL device formed of a conductive glass transparent anode, a hole transporting layer of 1,1-bis(4-p-tolylaminophenyl) cyclohexane, an electron transporting layer of 4,4'-bis(5,7-di-tert-pentyl-2-benzoxyzolyl)stilben, and an indium cathode. In U.S. Pat. No. 6,229,012, the disclosure of which is totally incorporated herein by reference, there are illustrated devices with certain carbazoles.

U.S. Pat. No. 4,720,432, the disclosure of which is totally incorporated herein by reference, discloses an organic EL device comprising a dual-layer hole injecting and transporting zone, one layer being comprised of porphyrinic compounds supporting hole injection and the other layer being comprised of aromatic tertiary amine compounds supporting hole transport.

U.S. Pat. No. 4,769,292, the disclosure of which is totally incorporated herein by reference, discloses an EL device employing a luminescent zone comprised of an organic host material capable of sustaining hole-electron recombination and a fluorescent dye material capable of emitting light in response to energy released by hole-electron recombination. One host material disclosed in the '292 patent is an aluminum complex of 8-hydroxyquinoline, and more specifically, tris(8-hydroxyquinolinate)aluminum.

U.S. Pat. No. 5,409,783, the disclosure of which is totally incorporated herein by reference, discloses a red-emitting organic EL device containing a dopant of a tris(8-hydroxyquinolinate)aluminum with a red fluorescent dye. Further, blue-emitting organic EL devices are illustrated in, for example, U.S. Pat. Nos. 5,151,629 and 5,516,577, the disclosures of which are totally incorporated herein by reference.

While progress in organic EL research has elevated the potential of organic EL devices for widespread applications, the performance levels of a number of devices are still below expectations in several instances. Further, for visual display applications, organic luminescent materials should provide a satisfactory color in the visible spectrum, normally with emission maxima at about 460, 550 and 630 nanometers for blue, green and red. Moreover, although the use of aromatic tertiary amines as hole transport materials in organic EL devices is known, the amine compounds selected, such as N,N,N',N'-tetraarylbenzidines, have a tendency to form complexes with the EL electron transport materials in contact therewith, thus resulting in, for example, emission with a broad spectra. This complexation for blue emitting devices results in the electron transport materials retaining a larger band gap than those used in devices with green or red emission. Thus, there continues to be a need for hole transport compositions for organic EL devices, and which materials are suitable for selection in blue emitting devices. Also, there is a need for EL hole transports which are vacuum evaporable and form films with excellent thermal stability. There is also a need for luminescent compositions which are capable of providing uniform and satisfactory emission in the visible spectrum from blue to red colors. In particular, there is a need for efficient blue luminescent materials for organic EL devices, which can be doped with a fluorescent dye to provide different colors by a downhill energy transfer process. Further there is also a need for luminescent compositions which can enhance the EL charge transporting characteristics thus lowing device driving voltages. Therefore, one feature disclosed herein is to provide charge transport/luminescent materials comprised of a new class of carbazole compounds and wherein there is avoided or there is minimized poor film forming properties, thermal instability, and weaker fluorescent properties.

BRIEF DESCRIPTION OF THE DRAWINGS

Illustrated in FIGS. 1, 2, 3 and 4 are embodiments of the electroluminescent devices of the present invention.

SUMMARY

Figure 1:
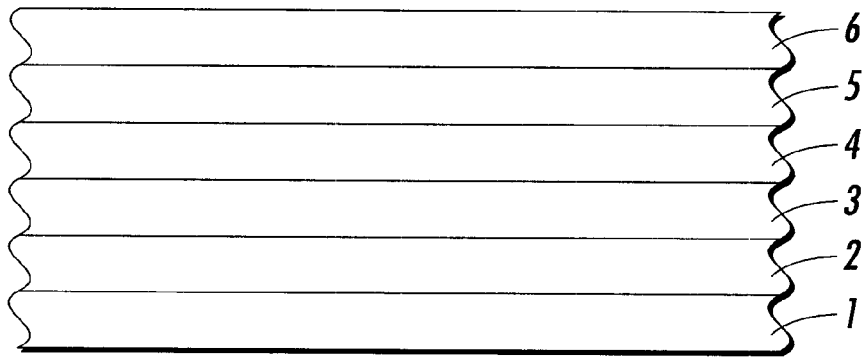

It is a feature of the present invention to provide new charge transport compositions for organic EL devices.

In another feature of the present invention there is provided organic EL devices with a light emitting layer containing a luminescent material comprised of novel carbazole compounds.

It is another feature of the present invention to provide organic EL devices with several advantages, such as low operation voltages, and uniform light emission with spectrum spreading from blue to longer wavelengths.

Yet in a further feature of the present invention there are provided organic EL devices comprised of a supporting substrate of, for example, glass, an anode, an optional buffer layer of, for example, copper phthalocyanine, a hole transporting layer comprised of a carbazole illustrated herein, an electron transporting layer comprised of, for example, a triazine compound, and in contact therewith a low work function metal, such as a cathode, wherein light emission may originate from the carbazole layer, the electron transport layer, or both layers thereof.

Moreover, in a feature of the present invention there are provided organic EL devices comprised of a supporting substrate of, for example, glass, an anode, an optional buffer layer of, for example, copper phthalocyanine, a hole injection-assistant layer comprised of, for example, a N,N,N',N'-tetraarylbenzidine compound, a carbazole hole transporting layer, an electron transporting layer comprised of, for example, a triazine compound, and in contact therewith a low work function metal, such as a cathode, and wherein light emission may originate from the carbazole layer, the electron transport layer, or both layers thereof.

Disclosed herein are devices comprised of a supporting substrate of, for example, glass, an anode, an optional buffer layer of, for example, copper phthalocyanine, a hole injection-assistant layer comprised of, for example, a N,N,N',N'-tetraarylbenzidine compound, a hole transporting layer comprised of a novel carbazole compound, an electron transporting layer comprised of, for example, a triazine compound, an organic electron injecting-assistant layer comprised of, for example, tris(8-hydroxyquinolinato) aluminum, and in contact therewith a low work function metal cathode, wherein light emission may originate from the carbazole layer, the electron transport layer, or both layers thereof; and organic EL devices comprised of a supporting substrate of, for example, glass, an anode, a buffer layer of, for example, copper phthalocyanine, a hole injection-assistant layer comprised of, for example, a N,N,N',N'-tetraarylbenzidine compound, a hole transporting layer comprised of a carbazole compound illustrated herein of the formulas recited herein, an organic light emitting layer comprised of, for example, a fluorescent anthracene compound, an electron transporting layer comprised of, for example, tris(8-hydroxyquinolinato)aluminum, and in contact therewith a cathode.

Illustrated herein is a class of charge transport/luminescent materials comprised of carbazole compounds of the formula

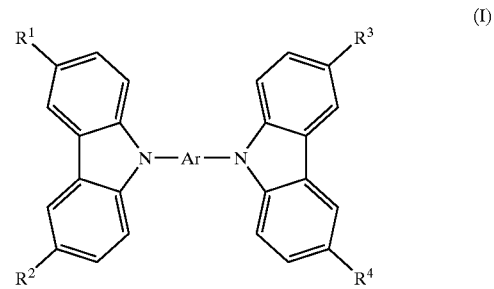

wherein $R^1$, $R^2$, $R^3$, and $R^4$ are each a non-hydrogen substituent, which may be individually selected from the group consisting of an alkyl with, for example, (for the number ranges recited herein there is envisioned that other numbers outside the ranges indicated may be acceptable) 1 to about 10 carbon atoms, an alkoxyl group containing from 1 to about 6 carbon atoms, a hydrocarbon aryl group containing, for example, from about 6 to about 60 carbon atoms and, more specifically, from about 6 to about 30 carbon atoms, or a heteroaromatic group, wherein the alkyl or alkoxyl group may be selected from the group consisting of a methyl, a butyl, a cyclohexyl, a methoxy, and the like; wherein the hydrocarbon aryl group can be independently selected, for example, from the group consisting of a phenyl, a stilbenyl, a biphenylyl, a naphthyl, an anthryl and the like; wherein the hydrocarbon aryl group may further possess a substituent of, for example, an alkyl with from 1 to about 6 carbon atoms, a alkoxy group containing from 1 to about 6 carbons, and the like; the heteroaromatic group may contain from about 2 to about 30 carbon atoms, and which group may be independently selected from the group consisting of a thienyl, a carbozolyl, a quinolyl, and the like; wherein Ar is a bivalent aromatic group of, for example, an arylene with from about 6 to about 30 carbon atoms, or a heteroaromatic divalent group.

Illustrative examples of the divalent aromatic group follow

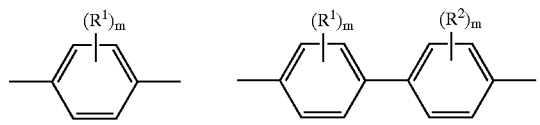

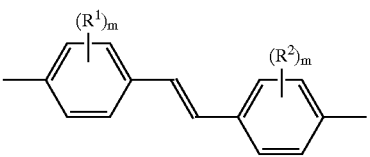

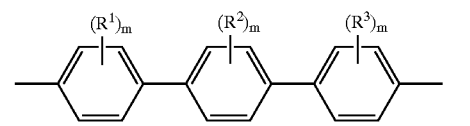

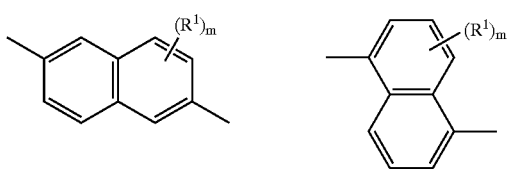

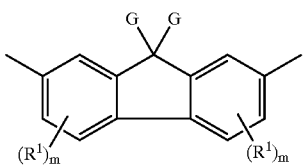

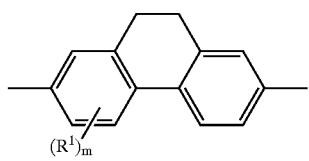

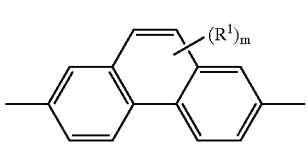

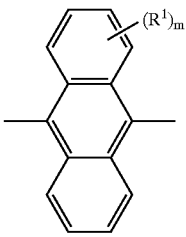

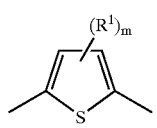

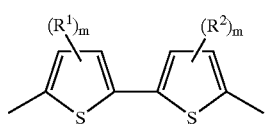

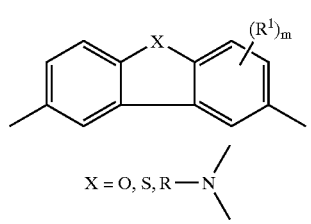

X = O, S, R—N

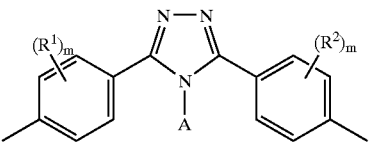

wherein $R^1$, $R^2$ and $R^3$ are independently a substituent group, which can be selected from the group consisting of hydrogen, halogen, a cyan; a hydrocarbyl of from 1 to about 20 carbons, a hydrocarbyl of from about 5 to about 15 carbons, a hydrocarbyl of from 1 to about 20 carbons further containing one or more heteroatoms of oxygen, sulfur, silicon and like; specifically $R^1$, $R^2$ and $R^3$ can be selected from the group consisting of hydrogen, a halogen, such as fluorine, cyan, methyl, methoxy, ethoxy, propoxy, butoxy, and the like; m is an integer of from 1 to about 6; G is a hydrocarbyl of from 1 to about 20 carbons, or a hydrocarbyl of from 6 to about 18 carbons, a hydrocarbyl of from 1 to about 20 carbons further containing one or more heteroatoms of oxygen, sulfur, silicon and like; G is an alkyl with from about 1 to about 20 carbons, a phenyl; an alkylphenyl, an alkoxyphenyl and the like; also together the 9-carbon in fluorene G may form a ring structure with from 5 to about 18 members; X may be selected from the group consisting of an oxygen atom, a sulfur atom, an imine group substituted with a radical of R being selected from, for example, the group consisting of an alkyl with from 1 to about 6 carbon atoms, a phenyl, a naphthyl, and the like; and wherein A is an aryl group containing from about 6 to about 36 carbon atoms, which aryl may be, for example, independently selected from the group consisting of a phenyl, a tolyl, a naphthyl, and the like. Preferably, Ar is selected from the group consisting of a phenylene, a biphenyl-4,4'-diyl, a naphthalene, a stilben-4,4'-diyl, and the like.

A specific class of the carbazole compounds are illustrated by the following formula:

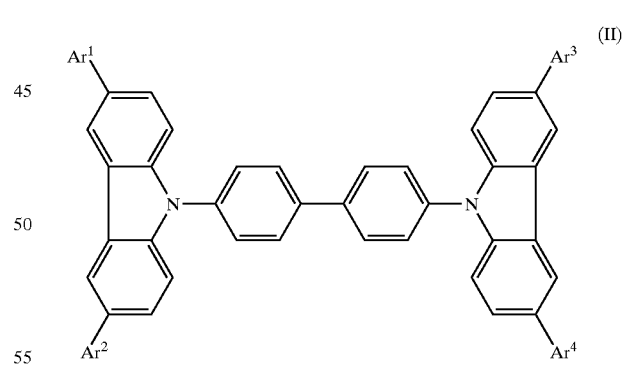

(II)

wherein $Ar^1$, $Ar^2$, $Ar^3$, and $Ar^4$ are each an aryl group with, for example, from about 6 to about 18 carbons, or a heteroaromatic group containing a heteroatom of, for example, oxygen, sulfur, nitrogen or silicon; wherein the aryl or heteoaromatic groups may further contain a substituent comprised of fluorine, cyan, an alkyl of from 1 to about 15 carbons, an alkoxyl containing from 1 to about 15 carbons, and the like. More specifically, $Ar^1$, $Ar^2$, $Ar^3$, and $Ar^4$ are selected from the group consisting of phenyl, a tolyl, a xylyl, a methyoxyphenyl, a fluorophenyl, a stilbenyl, a biphenylyl, a naphthyl, an anthyl group and the like.

Illustrated herein are EL devices that are comprised in the following sequence of a supporting substrate of, for example, glass, an anode, an optional buffer layer, an organic hole transporting layer, an organic light emitting layer, and an optional electron transporting layer, and in contact therewith a low work function metal wherein the hole transport layer contains at least one carbazole compound illustrated by Formulas I and II; layered EL devices with a light emitting layer comprised of a luminescent composition comprised of a carbazole compound illustrated by Formulas I and II; layered EL devices with a light emitting layer comprised of a luminescent composition comprised of a carbazole compound illustrated by formulas I and/or II as a host component capable of sustaining hole-electron recombination and a guest fluorescent or phosphorescent material capable of emitting light in response to energy released by the hole-electron recombination. The light emitting layer may be formed by vacuum deposition from the simultaneous evaporation of the host material and the fluorescent/phosphorescent material. The presence of the fluorescent/phosphorescent material permits, for example, a wide latitude of wavelengths of light emission and may enable the enhancement of electroluminescent efficiency and excellent device operation stability.

The charge transport/luminescent carbazole materials illustrated herein possess in embodiments several advantages. For example, the carbazole compounds possess excellent charge transport properties; exhibit strong fluorescence in the solid state in the region of, for example, from about 400 nanometers to longer wavelengths of, for example, about 600 nanometers, and in particular in the blue region of about 400 nanometers to about 490 nanometers; possess the ability of forming films with excellent thermal stability by vacuum evaporation; and can also be blended with numerous fluorescent materials to form a common phase.

EMBODIMENTS

Illustrative examples of embodiments disclosed are illustrated with reference to FIGS. 1, 2, 3, and 4.

FIG. 1 illustrates an EL device or an organic light emitting diode, which is comprised of a supporting substrate 1 of, for example, glass, an anode 2 of, for example, an indium tin oxide layer in a thickness of, for example, from about 1 to about 500 nanometers, and more specifically, from about 30 to about 100 nanometers, an optional buffer layer 3 of, for example, copper phthalocyanine in a thickness of from about 5 to about 300 nanometers, and more specifically, from about 10 to about 100 nanometers, a hole transporting layer 4 comprised of the carbazole compound illustrated herein, which layer can be of a layer thickness of from about 1 to about 200 nanometers, and more specifically, from about 5 to about 100 nanometers, an electron transporting layer 5 comprised of, for example, a triazine compound, in a layer thickness of from about 5 to about 300 nanometers, and more specifically, from about 10 to about 100 nanometers, and in contact therewith a low work function metal such as a cathode 6. In this device, light emission may originate from the carbazole layer, the electron transport layer, or both of the aforementioned layers thereof.

Figure 2:
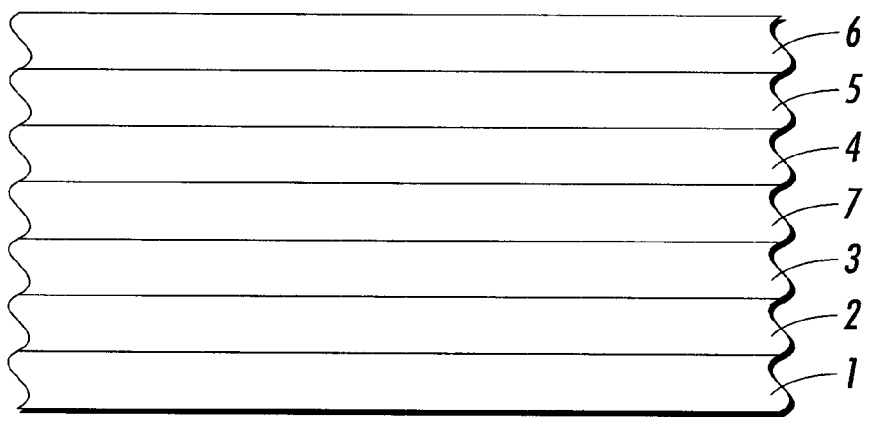

Illustrated in FIG. 2, is an EL device or an organic light emitting diode comprised of a supporting substrate 1 of, for example, glass, anode 2 of, for example, an indium tin oxide layer in a layer thickness of from about 1 to about 500 nanometers, and more specifically, from about 30 to about 100 nanometers, an optional buffer layer 3 of, for example, copper phthalocyanine in a layer thickness of from about 5 to about 300 nanometers, more specifically, from about 10 to about 100 nanometers, a hole injection-assistant layer 7 comprised of, for example, a N,N,N',N'-tetraarylbenzidine compound in a layer thickness of from about 1 to about 200 nanometers, and more specifically, from about 5 to about 100 nanometers, a hole transporting layer 4 comprised of the carbazole compound of the formulas illustrated herein, which layer can be of a thickness of from about 1 to about 200 nanometers, and more specifically, from about 5 to about 100 nanometers, an electron transporting layer 5 comprised of, for example, a triazine compound, in a layer thickness of from about 5 to about 300 nanometers, and more specifically, from about 10 to about 100 nanometers, and in contact therewith a low work function metal cathode 6. A primary purpose of the hole injecting-assistant layer is to build up a stepwise energy level to assist in hole injection from the anode into the hole transport carbazole layer, thus reducing the driving voltage of the device. In this device, light emissions may originate from the carbazole layer, the electron transport layer, or both layers thereof.

Figure 3:
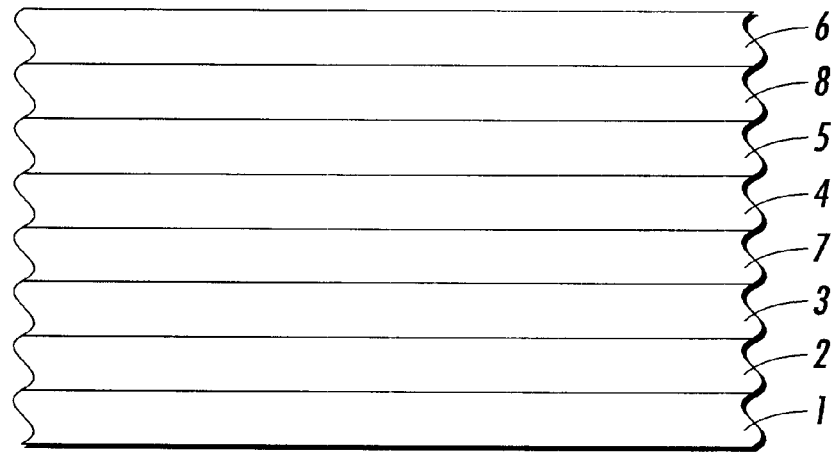

Illustrated in FIG. 3, is a light emitting diode comprised of a supporting substrate 1 of, for example, glass, an anode 2 of, for example, an indium tin oxide layer in a layer thickness of from about 1 to about 500 nanometers, and more specifically, from about 30 to about 100 nanometers, a optional buffer layer 3 of, for example, copper phthalocyanine in a layer thickness of from about 5 to about 300 nanometers, and more specifically, from about 10 to about 100 nanometers, a hole injection-assistant layer 7 comprised of, for example, a N,N,N',N'-tetraarylbenzidine compound in a layer thickness of from about 1 to about 200 nanometers, and more specifically, from about 5 to about 100 nanometers, a hole transporting carbazole layer 4, which layer can be of a thickness of from about 1 to about 200 nanometers, and more specifically, from about 5 to about 100 nanometers, an electron transporting layer 5 comprised of, for example, a triazine compound in a layer thickness of from about 5 to about 300 nanometers, and more specifically, from about 10 to about 100 nanometers, an organic electron injecting-assistant layer 8 comprised of, for example, tris(8-hydroxyquinolinato)aluminum in a layer thickness of from about 5 to about 300 nanometers, and more specifically, from about 10 to about 100 nanometers, and in contact therewith a low work function metal cathode 6. A primary purpose of the electron injecting-assistant layer is to build up a stepwise energy level to assist in electron injections from the cathode into the electron transport layer, thus reducing the driving voltage of the device; and in particular providing a blue emitting device in which the band gap of the emitter molecule is larger than various nonblue color emitters, such as green emitting Alq3. In this device, light emission may originate from the carbazole layer, the electron transport layer, or both layers thereof.

Figure 4:
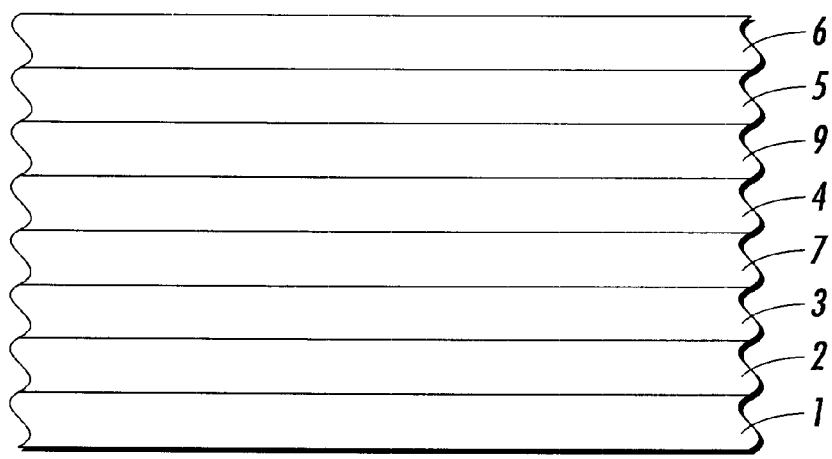

Illustrated in FIG. 4, is an EL device or an organic light emitting diode comprised of a supporting substrate 1 of, for example, glass, an anode 2 of, for example, an indium tin oxide layer in a layer thickness of from about 1 to about 500 nanometers, and more specifically, from about 30 to about 100 nanometers;, an optional buffer layer 3 of, for example, copper phthalocyanine in a layer thickness of from about 5 to about 300 nanometers, and more specifically, from about 10 to about 100 nanometers; a hole injection-assistant layer 7 comprised of, for example, a N,N,N',N'-tetraarylbenzidine compound in a layer thickness of from about 1 to about 200 nanometers, and more specifically, from about 5 to about 100 nanometers; a carbazole hole transporting layer 4, which layer can be in a thickness of from about 1 to about 200 nanometers, and more specifically, from about 5 to about 100 nanometers; an organic light emitting layer 9 comprised of, for example, a fluorescent anthracene compound in a layer thickness of from about 5 to about 300 nanometers, and more specifically, from about 10 to about 80 nanometers; an electron transporting layer 5 comprised of, for example, tris(8-hydroxyquinolinato)aluminum in a layer thickness of from about 5 to about 300 nanometers, and more specifically, from about 10 to about 100 nanometers, and in contact therewith a cathode 6.

In embodiments illustrated herein there is provided an organic electroluminescent device comprised of a first electrode, such as anode and a second electrode, such as a cathode, and an EL element positioned between the anode and the cathode, wherein the EL element has at least a layer comprised of a carbazole compound illustrated by the formula

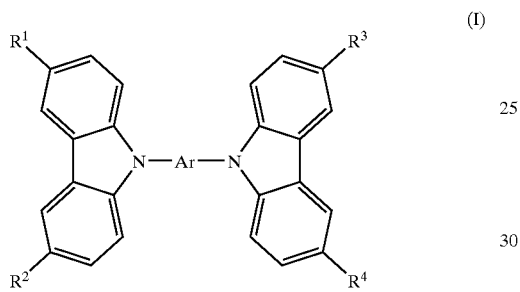

(I)

wherein $R^1$, $R^2$, $R^3$, and $R^4$ are each a non-hydrogen substituent, which may be individually selected from the group consisting of an alkyl with, for example, (as appropriate all carbon chain lengths, and substituent examples may be other than those disclosed) 1 to about 10 carbon atoms; an alkoxyl group containing, for example, from 1 to about 6 carbon atoms; a hydrocarbon aryl group containing, for example, from about 6 to about 60 carbon atoms, and more specifically, from about 6 to about 30 carbon atoms, or a heteroaromatic group; wherein the alkyl or alkoxyl group may be selected from the group consisting of a methyl, an ethyl, a propyl, a butyl, a cyclohexyl, a methoxy, an ethoxy, a propoxy, a butoxy and the like; wherein the hydrocarbon aryl group can be independently selected, for example, from the group consisting of a phenyl, a stilbenyl, a biphenylyl, a naphthyl, an anthryl and the like; wherein the hydrocarbon aryl group may further possess a substituent of, for example, an alkyl with from 1 to about 6 carbon atoms, a alkoxy group containing from 1 to about 6 carbons, and the like; the heteroaromatic group may contain from about 2 to about 30 carbon atoms, which may independently selected from the group consisting of a thienyl, a carbozolyl, a quinolyl, and the like; wherein Ar is a bivalent aromatic group of, for example, an arylene with from about 6 to about 36 carbon atoms, or a heteroaromatic divalent group. Illustrative examples of the divalent or bivalent aromatic group are

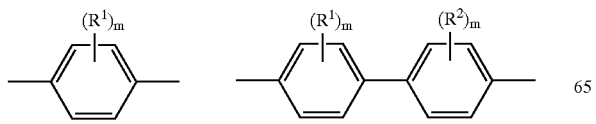

-continued

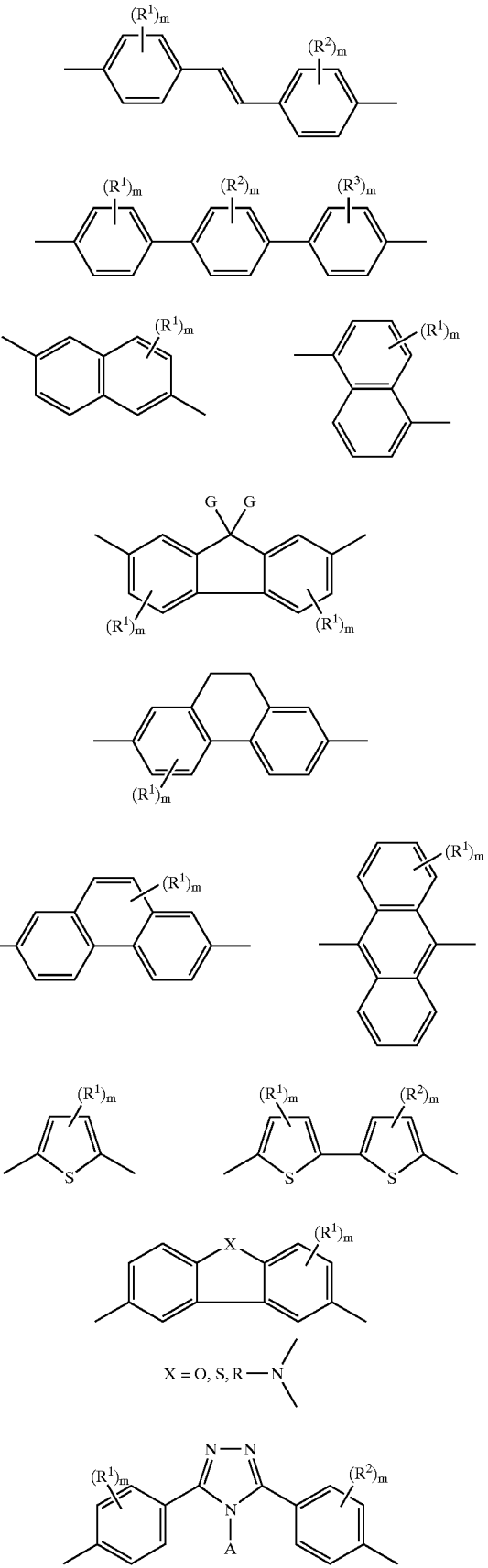

wherein $R^1$, $R^2$ and $R^3$ are independently a suitable substituent group, which can be selected from the group consisting of hydrogen, halogen, a cyan, a hydrocarbyl of from 1 to about 20 carbons, a hydrocarbyl of from 1 to about 20 carbons further containing one or more heteroatoms of oxygen, sulfur, silicon and like. Specifically, $R^1$, $R^2$ and $R^3$ can be selected from the group consisting of hydrogen, fluorine, cyan, methyl, methoxyl and the like; m is an integer of from 1 to about 6; G is a hydrocarbyl of from 1 to about 20 carbons, a hydrocarbyl of from 1 to about 20 carbons further containing one or more heteroatoms of oxygen, sulfur, silicon and like; preferably G is an alkyl with from about one to about 20 carbons, a phenyl, an alkylphenyl, an alkoxyphenyl and the like; further together the 9 carbon in fluorene G may form a ring structure with from 5 to about 18 members; X may be selected from the group consisting of an oxygen atom, a sulfur atom, an imine group substituted with an R being selected from the group consisting of an alkyl with from 1 to about 6 carbon atoms, a phenyl, a naphthyl, and the like; and wherein A is an aryl group containing from about 6 to about 30 carbon atoms, which may be independently selected from the group consisting of a phenyl, a tolyl, a naphthyl, and the like. Preferably, Ar is selected from the group consisting of a phenylene, a biphenyl-4,4'-diyl, a naphthalene, a stilben-4,4'-diyl, and the like. Examples of $R^1$, $R^2$, $R^3$, and $R^4$ include a phenyl, p-tolyl, m-tolyl, xylyl, p-methoxyphenyl, m-methoxyphenyl, p-fluorophenyl, m-fluorophenyl, p-trifluoromethylphenyl m-trifluoro methylphenyl, m-cyanophenyl, p-cyanophenyl, and the like; a naphthyl, such as 1-naphthyl, 2-naphthyl and the like; a phenylvinyl, and the like. Preferred examples of Ar include 1,1'-biphenyl-4,4'-diyl, stilbene-4,4'-diyl, 2,8-naphthalene, anthracene-9,10-diyl and the like.

A specific class of the carbazole compounds of the present invention is illustrated by the following formulas

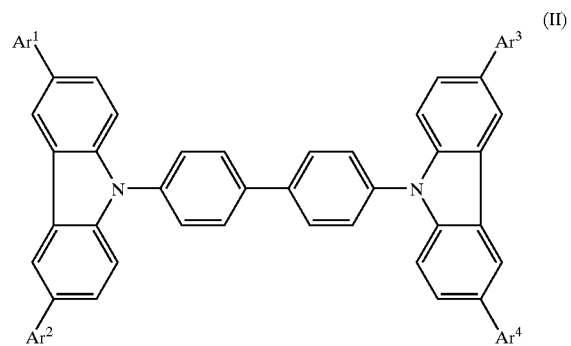

wherein $Ar^1$, $Ar^2$, $Ar^3$, and $Ar^4$ are each an aryl group with from about 6 to about 20 carbons, or heteroaromatic group containing a heteroatom of oxygen, sulfur, nitrogen or silicon; wherein said aryl or heteoaromatic group may further have a substituent comprised of fluorine, cyan, an alkyl of from 1 to about 15 carbons, an alkoxyl containing from 1 to about 15 carbons, and the like. Preferably, $Ar^1$, $Ar^2$, $Ar^3$, and $Ar^4$ are selected from the group consisting of phenyl, a tolyl, a xylyl, a methyoxyphenyl, a fluorophenyl, a stilbenyl, a biphenylyl, a naphthyl, an anthyl group and the like.

Specific examples of carbazole compounds selected for the EL devices illustrated herein are

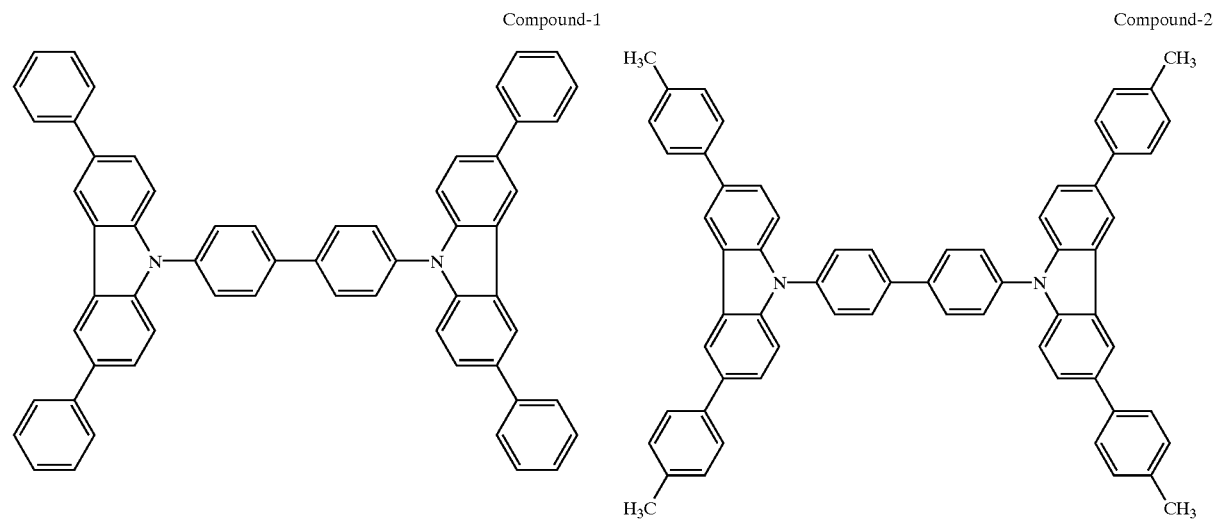

-continued
Compound-3 Compound-4
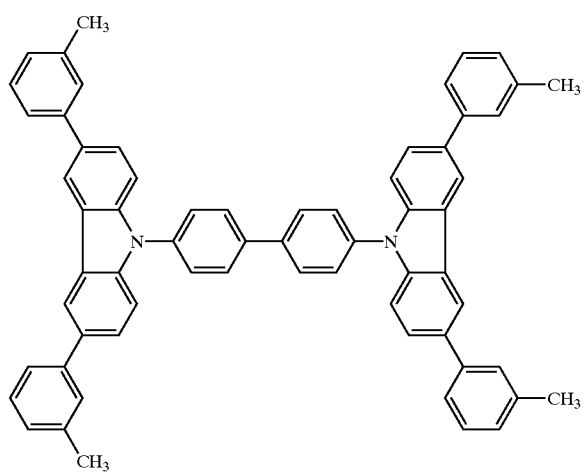
Compound-5 Compound-6
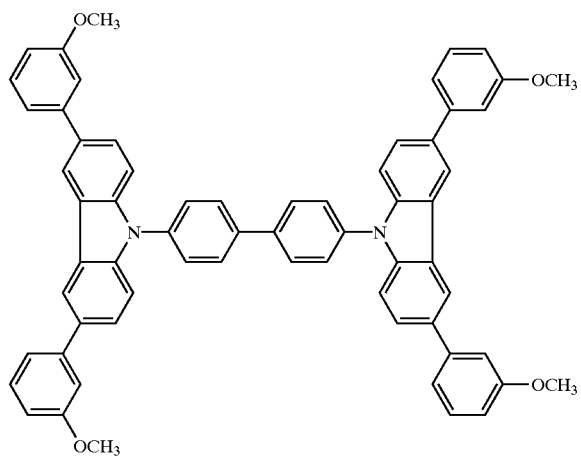
Compound-7 Compound-8
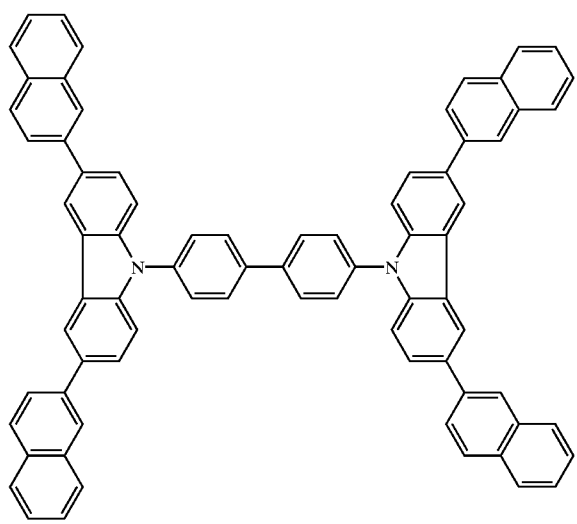

Compound-9
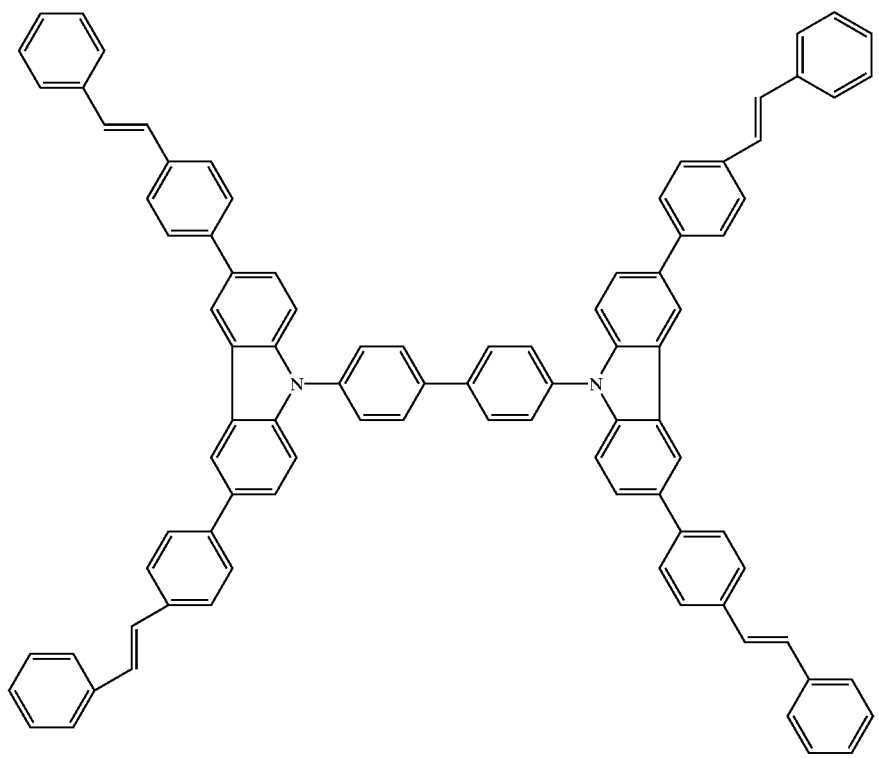
Compound-10
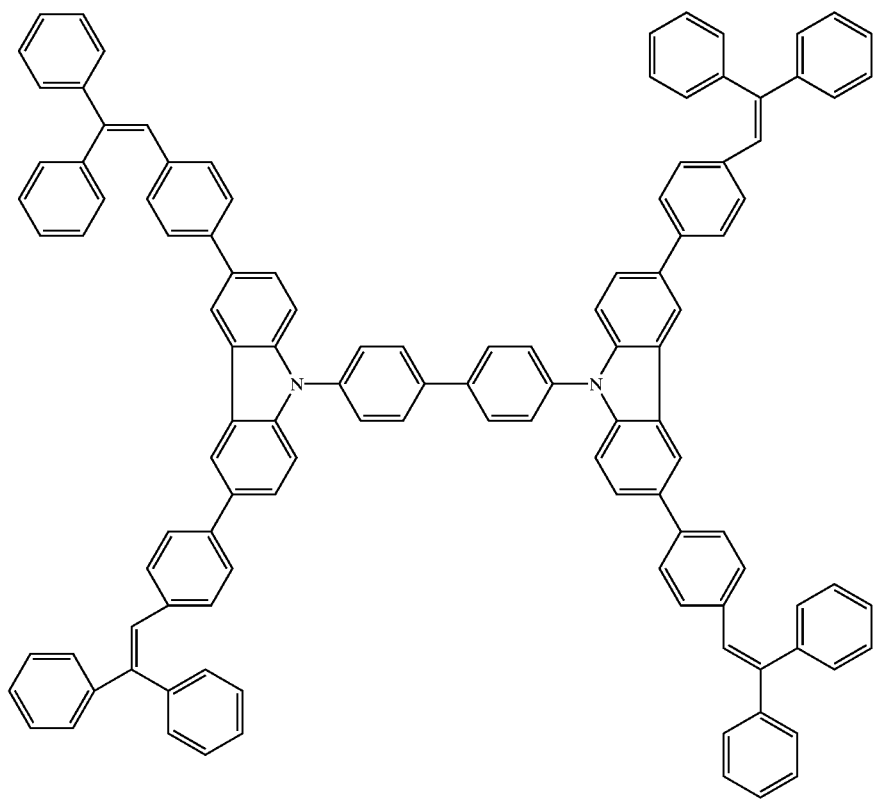

Compound-11

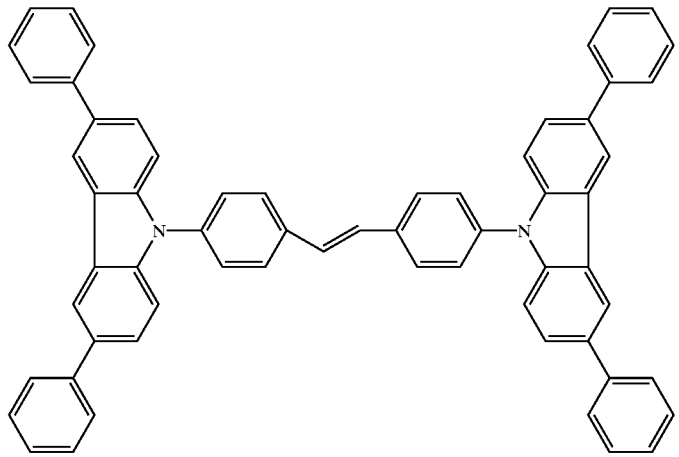

The carbazole hole transport layer may be formed by any convenient suitable manner. For example, it can be prepared by vacuum deposition from the evaporation of the carbazole material. The thickness of the carbazole layer is not particularly limited, and can range from, for example, from about 5 nanometers to about 300 nanometers, and preferably from about 10 nanometers to about 100 nanometers.

In embodiments it is desirable that the organic EL devices comprise a supporting substrate. Illustrative examples of the supporting substrate include polymeric components, glass and the like, and polyesters like MYLAR®, polycarbonates, polyacrylates, polymethacrylates, polysulfones, quartz, and the like. Other substrates can also be selected provided the material chosen can effectively support the other layers, and that the substrate does not substantially interfere with the device functional performance. The thickness of the substrate can be, for example, from about 25 to about 5,000 microns or more, and for example, from about 50 to about 3,000 depending, for example on the structural demands of the device.

Examples of the anode, such as anode 2, which is contiguous to the substrate, include positive charge injecting electrodes, such as indium tin oxide, tin oxide, gold, platinum, or other materials such as electrically conductive carbon, with a work function equal to, or greater than about 4 electron volts, and more specifically, from about 4 to about 6 electron volts. The thickness of the anode can range from about 1 to about 5,000 nanometers with the preferred range being dictated by the optical constants of the anode material. One preferred range of thickness for the electrode, such as the anode, is from about 30 to about 100 nanometers.

The buffer layer illustrated herein is optional. Functions of this layer are primarily to facilitate efficient injection of holes from the anode, and to improve the adhesion between the anode and the organic hole transporting layer, thus further improving the device operation stability in embodiments. Examples of buffer layer materials include conductive materials, such as polyanilines and their acid-doped forms, polythiophenes and their acid-doped forms, polypyrrole, poly(phenylene vinylene), amorphous graphite or carbon and the like. Preferred materials used in the buffer layer are hole transport molecules. Specific examples of such hole transport materials are porphyrin derivatives, such as those disclosed in U.S. Pat. No. 4,356,429, the disclosure of which is totally incorporated herein by reference, including 1,10,15,20-tetraphenyl-21H,23H-porphyrin copper (II), copper phthalocyanine, copper tetramethyl phthalocyanine, zinc phthalocyanine, titanium oxide phthalocyanine, magnesium phthalocyanine and the like. The buffer layer can be prepared by forming one of the buffer compounds into thin film by known methods, such as by vapor deposition or spin coating. The thickness of buffer layer thus formed is not particularly limited, and can be from, for example, about 5 nanometes to about 300 nanometers, and preferably from about 10 nanometers to about 100 nanometers.

The hole injection-assistant layer can be formed of various suitable known materials, such as aromatic tertiary amines such as those disclosed in U.S. Pat. No. 4,539,507, the disclosure of which is totally incorporated herein by reference. Suitable exemplary aromatic tertiary amines include, but are not limited to, bis(4-dimethylamino-2-methylphenyl)phenylmethane, N,N,N-tri(p-tolyl)amine, 1,1-bis(4-di-p-tolylaminophenyl)cyclohexane, 1,1-bis(4-di-p-tolylaminophenyl)-4-phenyl cyclohexane, N,N'-diphenyl-N,N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl-4,4'-diamine, N,N,N',N'-tetra-p-tolyl-1,1'-biphenyl-4,4'-diamine, N,N'-bis(1,1'-biphenyl-4-yl)-N,N'-diphenyl-1,1'-biphenyl-4, 4'-diamine, N,N,N',N'-tetrakis(1, 1'-biphenyl-4-yl)-1,1'-biphenyl-4,4'-diamine, N,N'-di-1-naphthyl-N,N'-diphenyl-1,1'-biphenyl-4,4'-diamine, N,N,N', N'-tetra-1-naphthyl-1,1'-biphenyl-4,4'-diamine, mixtures thereof and the like; polynuclear aromatic amines, examples of which include polynuclear aromatic amines like N,N-bis-[4'-(N-phenyl-N-m-tolylamino)-4-biphenylyl]aniline, N,N- bis-[4'-(N-phenyl-N-m-tolylamino)-4-biphenylyl]-m-toluidine, N,N-bis-[4'-(N-phenyl-N-m-tolylamino)-4-biphenylyl]-p-toluidine, N,N-bis-[4'-(N-phenyl-N-p-tolylamino)-4-biphenylyl]aniline, N,N-bis-[4'-(N-phenyl-N-p-tolylamino)-4-biphenylyl]-m-toluidine, N,N-bis-[4'-(N-phenyl-N-p-tolylamino)-4-biphenylyl]-p-toluidine, N,N-bis-[4'-(N-phenyl-N-p-chlorophenylamino)-4-biphenylyl]-m-toluidine, N,N-bis-[4'-(N-phenyl-N-m-chlorophenylamino)-4-biphenylyl]-m-toluidine, N,N-bis-[4'-(N-phenyl-N-m-chlorophenylamino)-4-biphenylyl]-p-toluidine, N,N-bis-[4'-(N-phenyl-N-m-tolylamino)-4-biphenylyl]-p-chloroaniline, N,N-bis-[4'-(N-phenyl-N-p-tolylamino)-4-biphenylyl]-m-chloroaniline, N,N-bis-[4'-(N-phenyl-N-m-tolylamino)-4-biphenylyl]-1-aminonaphthalene, mixtures thereof and the like.

A specific class of the hole transport materials which may be selected for the EL devices disclosed herein include the indolocarabazoles of, for example, 5,11-di-naphthyl-5,11-dihydroindolo[3,2-b]carbazole and 2,8-dimethyl-5,11-di-naphthyl-5,11-dihydroindolo[3,2-b]carbazole, and others as described in U.S. Pat. No. 5,942,340, the disclosure of which is totally incorporated herein by reference.

Any suitable appropriate known electron component may be selected for the electron transporting layer, such as layer 5. For blue emitting devices, it is preferred that the electron transport materials have a band gap in the blue region of, for example, from about 400 nanometers to about 550 nanometers. This layer can be been formed by known methods, such as by vacuum deposition, and wherein the layer thickness can be from about 1 nanometer to about 300 nanometers, and preferably from about 5 nanometers to about 100 nanometers. Illustrative examples of the electron transporting compounds include quinolines, such as those disclosed in Japanese patent application 1995-150137, triazine compounds such as those disclosed in U.S. Pat. No. 6,225,467, and metal chelates of 8-hydroxyquinoline as disclosed in U.S. Pat. Nos. 4,539,507; 5,151,629, and 5,150,006, the disclosures of each of which are totally incorporated herein by reference.

The electron injection assistant layer is optional, but is preferred for blue emitting devices. A primary purpose of this layer is to build up a stepwise energy level to assist electron injection from the cathode into the electron transport layer, thus reducing the driving voltage of the device. A number of suitable electron transport known in the art may be used for this layer. Illustrative examples of electron transport materials, which may be selected for the electron injection-assistant layer, include triazine compounds such as those disclosed in U.S. Pat. No. 6,225,467, the disclosure of which is totally incorporated herein by reference, and metal chelates of 8-hydroxyquinoline such as tris(8-hydroxyquinolinate) aluminum, a preferred one, tris(8-hydroxyquinolinate) gallium, bis(8-hydroxyquinolinate) magnesium, bis(8-hydroxyquinolinate) zinc, tris(5-methyl-8-hydroxyquinolinate)aluminum, tris(7-propyl-8-quinolinolato)aluminum, bis[benzo{f}-8-quinolinate]zinc, bis(10-hydroxybenzo[h]quinolinate)beryllium, and the like. Another class of preferred electron injecting compounds are the metal thioxinoid compounds, illustrated in U.S. Pat. No. 5,846,666, the disclosure of which is totally incorporated herein by reference. Illustrative examples of metal thioxinoid compounds include bis(8-quinolinethiolato)zinc, bis(8-quinolinethiolato)cadmium, tris(8-quinolinethiolato) gallium, tris(8-quinolinethiolato)indium, bis(5-methylquinolinethiolato)zinc, tris(5-methylquinolinethiolato)gallium, tris(5-methylquinolinethiolato)indium, bis(5-methylquinolinethiolato)cadmium, bis(3-methylquinolinethiolato)cadmium, bis(5-methylquinolinethiolato)zinc, bis[benzo{f}-8-quinolinethiolato]zinc, bis[3-methylbenzo{f}-8-quinolinethiolato]zinc, bis[3,7-dimethylbenzo{f}-8-quinolinethiolato]zinc, and the like. Preferred are bis(8-quinolinethiolato)zinc, bis(8-quinolinethiolato) cadmium, tris(8-quinolinethiolato)gallium, tris(8-quinolinethiolato)indium and bis[benzo{f}-8-quinolinethiolato]zinc.

Any suitable appropriate luminescent components may be selected for the light emitting layer, such as layer 9. A preferred class of luminescent materials are the fluorescent hydrocarbons. Illustrative examples of such hydrocarbons include fluorescent dyes containing fused rings, such as perylene, rubrene, anthracene, coronene, phenanthracene, pyrene and the like, as illustrated in U.S. Pat. No. 3,172,862, the disclosure of which is totally incorporated herein by reference, and their derivatives developed later on butadienes, such as 1,4-diphenylbutadiene, tetraphenylbutadiene, and stilbenes, and hydrocarbon dyes illustrated in U.S. Pat. Nos. 4,356,429; 5,516,577; 5,536,949; 5,972,247; 6,093,864, and 6,214,481, the disclosures of each of which are totally incorporated herein by reference.

The electrode, such as cathode, can be constructed of any suitable appropriate metal, including high, for example from about 4 eV to about 6 eV, or a low work function component, such as metals with, for example, an eV of from about 2.5 eV to about 4.0 eV (electron volts). The cathode can be derived from a combination of a low work function metal (less than or equal to about 4 eV) and at least one other metal. Effective proportions of the low work function metal to the second or other metal are from, for example, about 0.1 percent to about 99.9 percent by weight. Illustrative examples of low work function metals include alkaline metals, such as lithium or sodium, Group 2A or alkaline earth metals, such as beryllium, magnesium, calcium, or barium, and Group III metals including rare earth metals and the actinide group metals, such as scandium, yttrium, lanthanum, cerium, europium, terbium, or actinium. Lithium, magnesium and calcium are in embodiments the preferred low work function metals.

The thickness of cathode is from, for example, about 10 nanometers to about 500 nanometers. The Mg:Ag cathodes of U.S. Pat. No. 4,885,211 constitute one preferred cathode construction. Another preferred cathode construction is described in U.S. Pat. No. 5,429,884, wherein the cathodes are formed from lithium alloys with other high work function metals such as aluminum and indium.

Both the anode and the cathode can be of any convenient appropriate forms, such as for example, wherein a thin conductive layer can be coated onto a light transmissive substrate, for example, a transparent or substantially transparent glass plate or plastic film. The EL device can include a light transmissive anode formed from tin oxide or indium tin oxide coated on a glass plate. Also, very thin, for example less than about 200 Å, like 95 to about 100 light-transparent metallic anodes can be used, such as gold, palladium, and the like. In addition, transparent or semitransparent thin layers of conductive carbon or conjugated polymers, such as polyaniline, polypyrrole, and the like, can be used as anodes. Any light transmissive polymeric film can be employed as the substrate.

Aspects illustrated herein include an electroluminescent device comprised of electrodes, such as an anode, a cathode, and situated between the anode and the cathode a carbazole layer of the formula

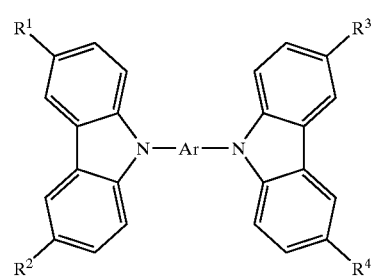

wherein $R^1$, $R^2$, $R^3$, and $R^4$ are independently selected from the group consisting of a hydrocarbyl, and wherein Ar is an aryl; an electroluminescent device comprised of a first electrode, a second electrode, and an organic layer containing a carbazole compound illustrated by the formula

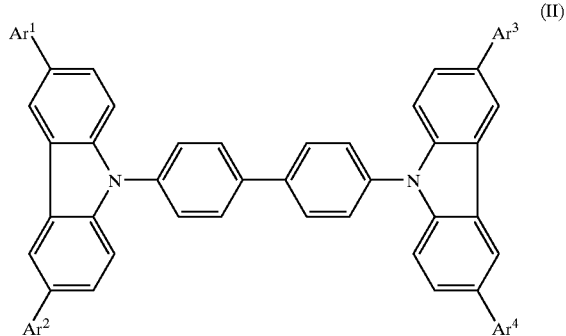

wherein $Ar^1$, $Ar^2$, $Ar^3$, and $Ar^4$ are each independently an aryl group with from about 6 to about 24 carbons; an electroluminescent device comprised in sequence of an anode, a hole transport layer, an electron transport layer, and a cathode, wherein the hole transport layer is comprised of a carbazole selected from the group consisting of a

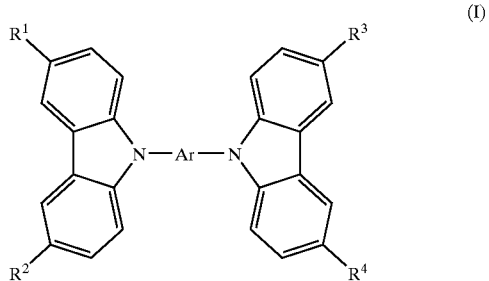

wherein $R^1$, $R^2$, $R^3$, and $R^4$ are independently selected from the group consisting of a hydrocarbyl, and wherein Ar is an aryl; and a

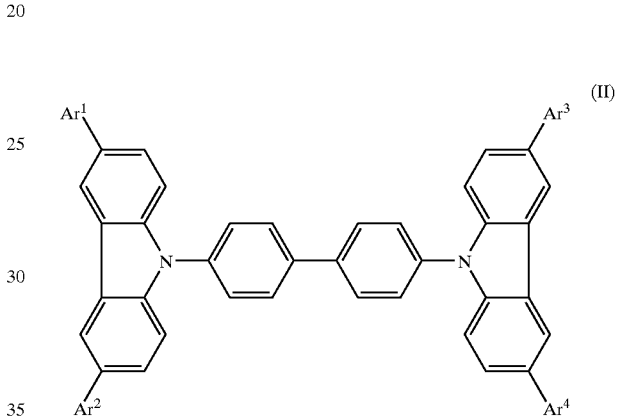

wherein $Ar^1$, $Ar^2$, $Ar^3$, and $Ar^4$ are each an aryl group with from about 6 to about 24 carbons; a device comprised of a first electrode, a second electrode, and a carbazole of the formula

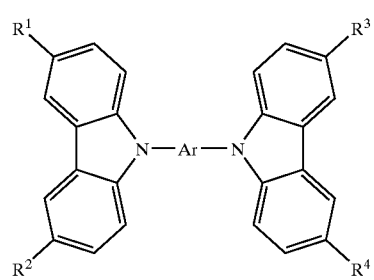

wherein $R^1$, $R^2$, $R^3$, and $R^4$ are independently selected from the group consisting of a hydrocarbyl, and wherein Ar is an aryl; and a hydrocarbyl containing a heteroatom of oxygen, sulfur, silicon, or nitrogen; or a heteroaromatic group containing a heteroatom of oxygen, sulfur, silicon, or nitrogen; a carbazole

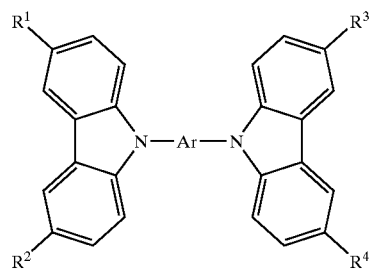
(I)
wherein $R^1$, $R^2$, $R^3$, and $R^4$ are independently a hydrocarbyl, and wherein Ar is an aryl; a carbazole compound of the formula
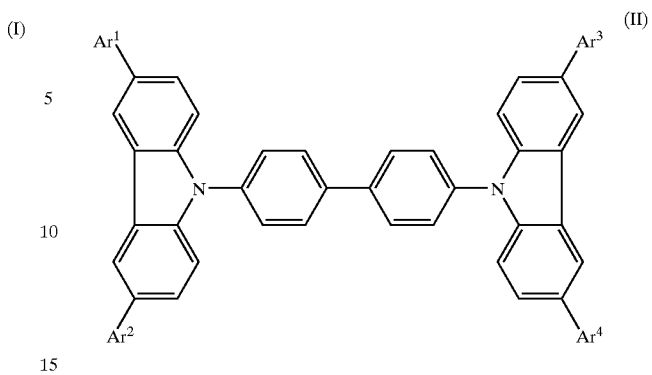
(II)
wherein $Ar^1$, $Ar^2$, $Ar^3$, and $Ar^4$ are each an aryl group with from about 6 to about 24 carbons; and a compound of the formulas as alternatively represented by
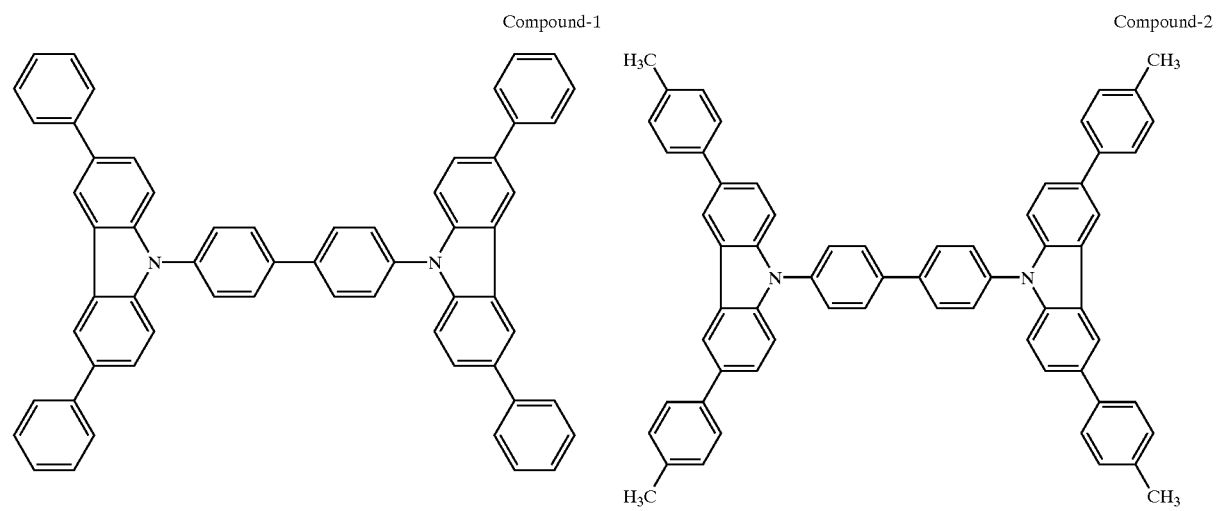
Compound-1
Compound-2
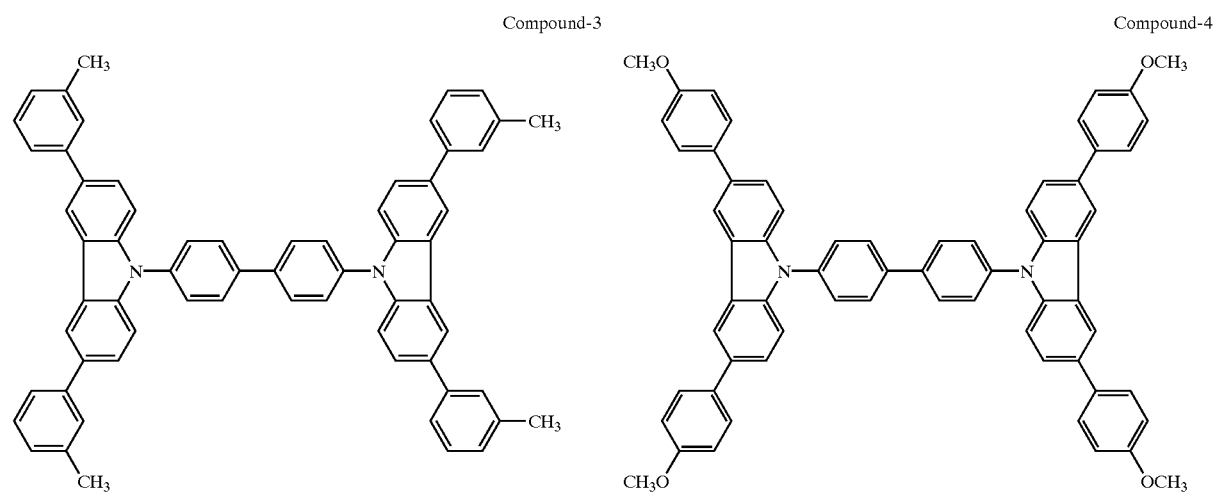
Compound-3
Compound-4

-continued
Compound-5
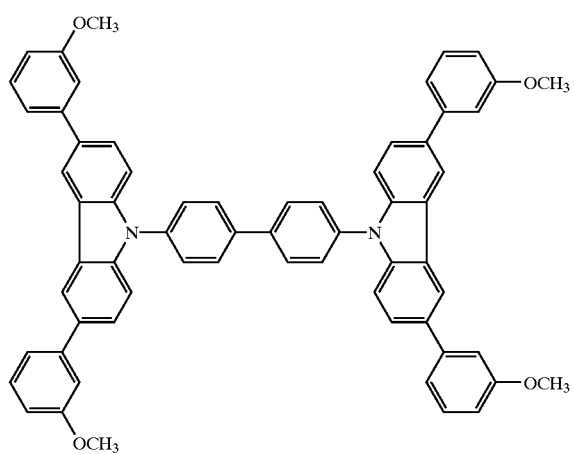
Compound-6
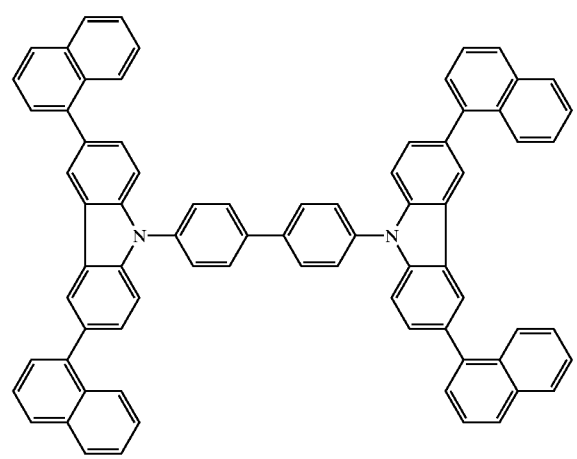
Compound-7
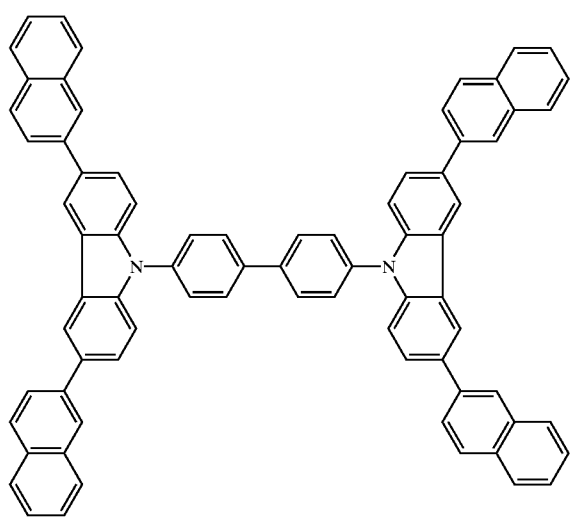
Compound-8
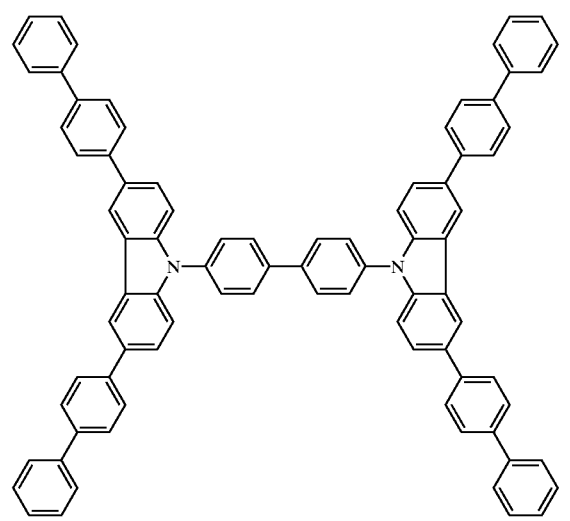
Compound-9
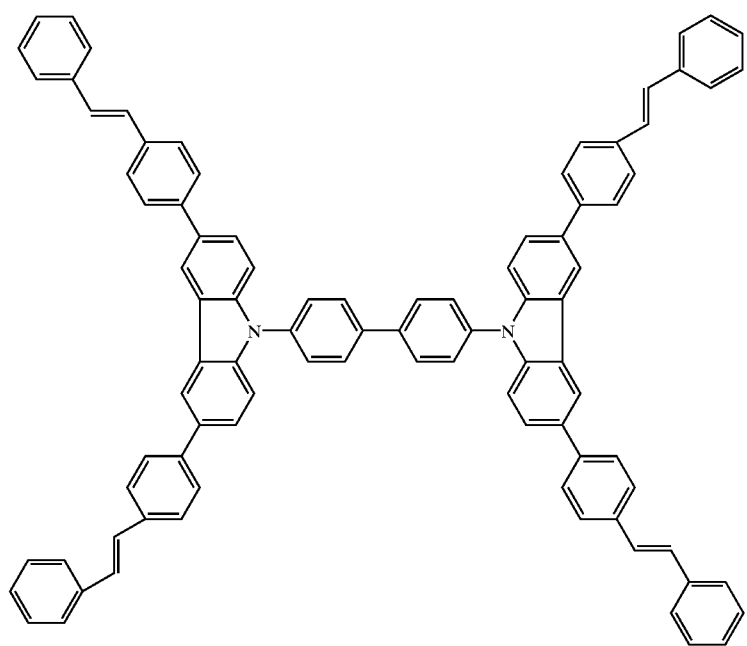

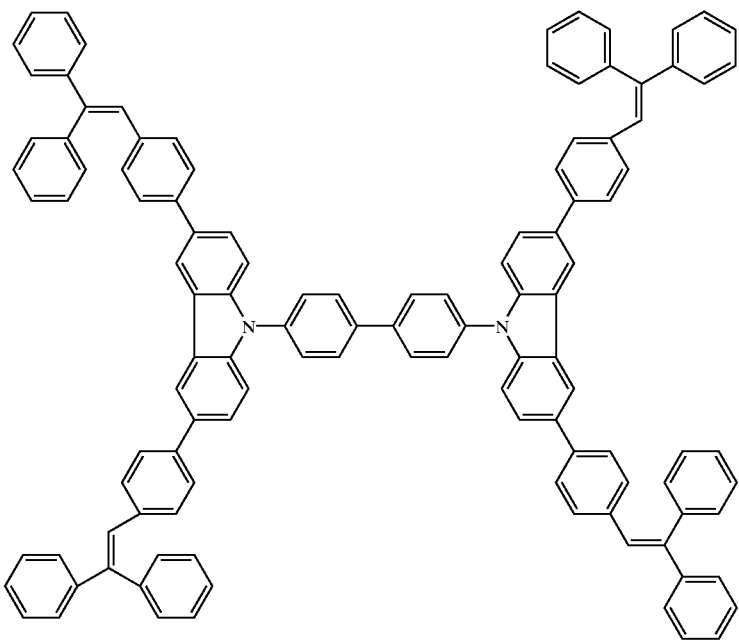

Compound-10

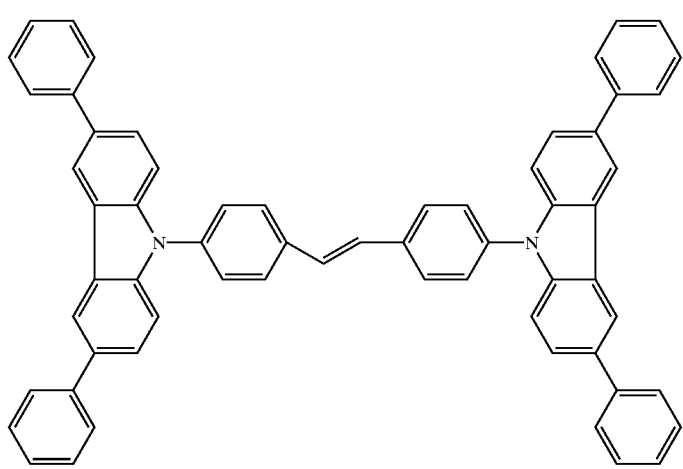

Compound-11

The following Examples are provided.

EXAMPLE I

Synthesis of 3,6-Diphenyl Carbazole

In a 250 milliliter round bottom flask there were added 3,6-dibromocarbazole (5 grams), 50 milliliters of 1,2-dimethoxyethane, phenylboric acid (4.8 grams) dissolved in ethanol, and sodium carbonate (4.2 grams) dissolved in 20 milliliters of water. After the resulting solution was saturated with argon, 0.49 gram of tetrakis-(triphenylphosphine) palladium was added. The reaction mixture was heated to reflux and stirred for 18 hours. The reaction flask was removed from the heat and cooled to room temperature, about 22° C. to about 25° C. The resulting solution was transferred to a separatory funnel, and the organic layer, which contained product, was separated from the aqueous phase. After removal of the organic solvents by evaporation, the residue was subjected to column chromatography on silica gel to yield 3.5 grams of 3,6-diphenyl carbazole as colorless powder product. Its chemical structure was confirmed by Proton IR analysis.

EXAMPLE II

Synthesis of 4,4'-Bis-[9-(3,6-diphenylcarbazolyl)]-1,1'-biphenyl (Compound 1):

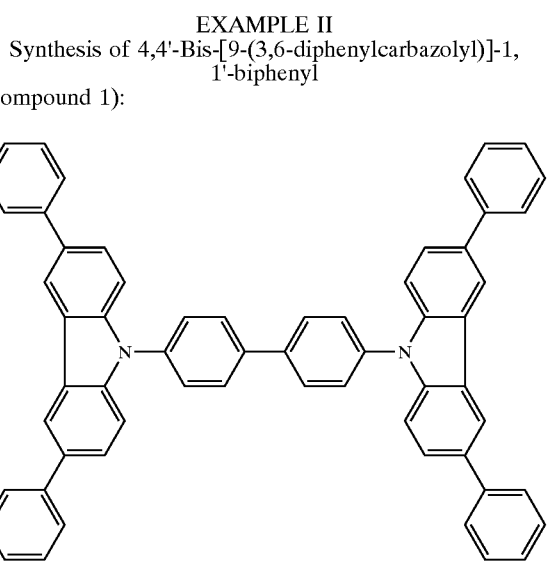

In a 50 milliliter round bottom flask there were added 4,4'-diiodo-1,1'-biphenyl (2.1 grams), 3,6-diphenyl carbazole (3.3 grams), potassium carbonate powder (1.4 grams), copper sulfate pentahydrate (0.06 grams), and 5 milliliters of tridecane. The resulting mixture was heated to 230° C. and stirred at this temperature under argon for 24 hours. After cooling to room temperature (~23° C.), the solids content resulting was ground into slurry, which slurry was then transferred to a filtration funnel, washed with hexane to remove the tridecane, followed by washing with 3 percent hydrochloric acid and water. The solid resulting was then dissolved in hot toluene. The insoluble residue was filtered hot. After cooling to room temperature, the product was crystallized from the solution to yield 2.3 grams of 4,4'-bis-[9-(3,6-diphenylcarbazolyl)]-1,1'-biphenyl as a yellowish powder. This compound had a melting point of 294° C. Its chemical structure was confirmed by proton analysis.

EXAMPLE III

An organic EL device with a structure similar to that of FIG. 3 was fabricated in the following manner:

1. A 500 Å indium tin oxide (ITO) anode coated glass substrate, the thickness of the glass substrate being about 1 millimeter, was cleaned with a commercial detergent, rinsed with deionized water and dried in a vacuum oven at 60° C. for 1 hour. Immediately before use, the glass was treated with UV ozone for 0.5 hour.

2. The ITO anode to be coated on the glass substrate was then placed in a vacuum deposition chamber. The deposition rate and layer thickness were controlled by an Inficon Model IC/5 controller. Under a pressure of about $5 \times 10^{-6}$ Torr, a 15 nanometer thick buffer was deposited on the ITO glass substrate and anode through simultaneous evaporation of copper phthalocyanine at a rate of 0.6 nanometer/second.

3. Onto the buffer layer was deposited a 30 nanometer thick hole transporting compound of N,N'-1-naphthyl-N,N'-diphenyl-1,1'-biphenyl-4,4'-diamine.

4. Onto the N,N'-1-naphthyl-N,N'-diphenyl-1,1'-biphenyl-4,4'-diamine layer there was deposited a 30 nanometer thick layer of 4,4'-bis(3,6-diphenylcarbazolyl-9-yl)-1,1'-biphenyl (as obtained from Example II) at a rate of 0.6 nanometer/second to form a light emitting layer.

5. A 12 nanometers thick electron transport layer was then deposited on layer 4 above by the evaporation of 1,4-bis[2-(4-phenylquinolyl)]benzene at a rate of 0.6 nanometer/second.

6. A 10 nanometers thick electron transport layer was then deposited by evaporation of tris(8-hydroxyquinolinato) aluminum at a rate of 0.6 nanometer/second to form an electron injection-assistant layer.

7. A 100 nanometer cathode of a magnesium silver alloy was deposited on layer 6 above at a total deposition rate of 0.5 nanometer/second by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The device as prepared above was retained in a dry box which was continuously purged with nitrogen gas. Its performance was assessed by measuring its current-voltage characteristics and light output under a direct current measurement. The current-voltage characteristics were determined with a Keithley Model 238 High Current Source Measure Unit. The ITO electrode was always connected to the positive terminal of the current source. At the same time, the light output from the device was monitored by a silicon photodiode.

When a direct current of 25 mA/cm$^2$ was applied to the above organic EL device there was provided a uniform blue light with an initial luminance of 200 Cd/m$^2$ (CIE color coordinates of X=0.146 and Y=0.078) as measured by the Minolta Chromameter CS-100).

EXAMPLE IV

An organic EL device was fabricated according to Example III except that to the 4,4'-bis(3,6-diphenylcarbazolyl-9-yl)-1,1'-biphenyl layer was added 1 percent (by weight) of a tert-butyl-substituted perylene fluorescent dye. This layer was deposited onto the N,N'-1-naphthyl-N,N'-diphenyl-1,1'-biphenyl-4,4'-diamine layer by the simultaneous evaporation from two independently controlled tantalum boats containing 4,4'-bis(3,6-diphenylcarbazolyl-9-yl)-1,1'-biphenyl and a tert-butyl-substituted perylene dye, respectively.

When a direct current of 25 mA/cm$^2$ was applied, the above prepared organic EL device provided a uniform blue light with an initial luminance of 380 Cd/m$^2$ as measured by the Minolta Chromameter CS-100).

EXAMPLE V

An organic EL device containing a 4,4'-bis(3,6-diphenylcarbazolyl-9-yl)-1,1'-biphenyl hole transport layer was fabricated in the following manner:

1. Under a pressure of about $5 \times 10^{-6}$ Torr, a 15 nanometer thick buffer was deposited on an ITO glass substrate of Example III by the simultaneous evaporation of copper phthalocyanine at a rate of 0.6 nanometer/second.

2. Onto the buffer layer was deposited a 30 nanometer thick hole transporting compound of N,N'-1-naphthyl-N,N'-diphenyl-1,1'-biphenyl-4,4'-diamine.

3. Onto the N,N'-1-naphthyl-N,N'-diphenyl-1,1'-biphenyl-4,4'-diamine layer there was deposited a 30 nanometer thick layer of 4,4'-bis(3,6-diphenylcarbazolyl-9-yl)-1,1'-biphenyl (as obtained from Example II) at a rate of 0.6 nanometer/second to form a light emitting layer.

4. Onto the hole transport layer 3 above a 15 nanometers thick light emitting layer was then deposited by evaporation of an anthracene compound at a rate of 0.6 nanometer/second.

5. A 10 nanometers thick electron transport layer was then deposited by evaporation of tris(8-hydroxyquinolinato) aluminum at a rate of 0.6 nanometer/second to form an electron transport layer.

6. A 100 nanometer cathode of a magnesium silver alloy was deposited at a total deposition rate of 0.5 nanometer/second onto the electron transport layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

When a direct current of 25 mA/cm$^2$ was applied, this organic EL device provided a uniform blue light with an initial luminance of 350 Cd/m$^2$ as measured by the Minolta Chromameter CS-100.

Other embodiments and modifications of the present invention may occur to those skilled in the art subsequent to a review of the information presented herein; these embodiments and modifications, equivalents thereof, substantial equivalents thereof, or similar equivalents thereof are also included within the scope of this invention.

What is claimed is:

1. An electroluminescent device comprised of an anode, a cathode, and situated between the anode and the cathode a carbazole layer of the formula

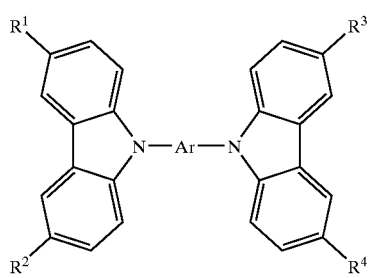

wherein $R^1$, $R^2$, $R^3$, and $R^4$ are independently selected from the group consisting of a hydrocarbyl, and wherein Ar is an aryl.

2. An electroluminescent device in accordance with claim 1 wherein said hydrocarbyl is an alkyl of from 1 to about 20 carbon atoms.

3. An electroluminescent device in accordance with claim 1 wherein said hydrocarbyl is an aryl of from about 6 to about 30 carbons.

4. An electroluminescent device in accordance with claim 1 wherein $R^1$, $R^2$, $R^3$, and $R^4$ are each selected from the group consisting of a methyl, a butyl, a cyclohexyl, a methoxy, an ethoxy, a butyloxy, dimethylamino, and diethylamino.

5. An electroluminescent device in accordance with claim 1 wherein $R^1$, $R^2$, $R^3$, and $R^4$ are each selected from the group consisting of a phenyl, a stilbenyl, a biphenylyl, a naphthyl, an anthryl, a thienyl, a carbozolyl, and a quinolyl.

6. An electroluminescent device in accordance with claim 1 wherein Ar is selected from the group consisting of

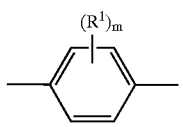 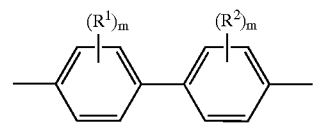

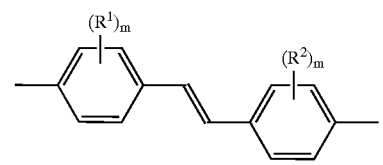

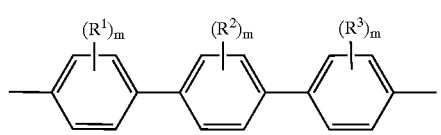

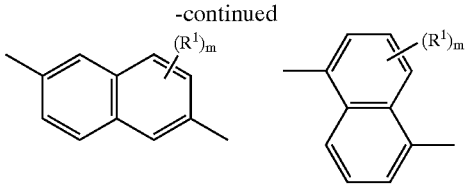

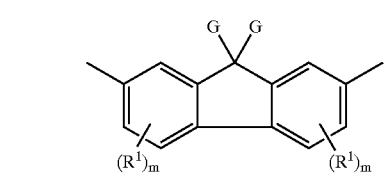

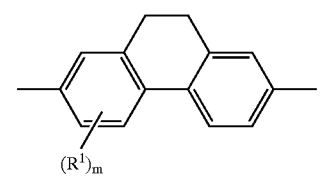

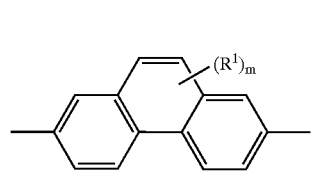 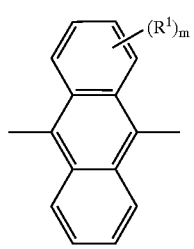

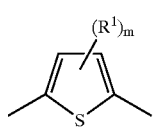 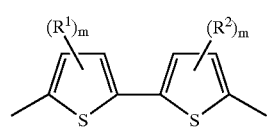

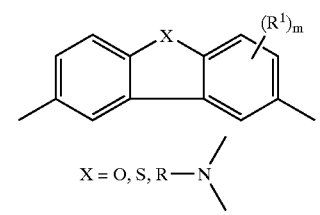

X = O, S, R—N

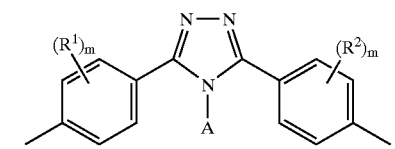

wherein $R^1$, $R^2$ and $R^3$ are independently a substituent group selected from the group consisting of hydrogen, halogen, a cyan, a hydrocarbyl of from 1 to about 20 carbons, optionally a hydrocarbyl of from 1 to about 20 carbons further containing one or more heteroatoms of oxygen, sulfur, nitrogen, and silicon; m is an integer or number of from 1 to about 6; G is a hydrocarbyl of from 1 to about 20 carbons, optionally a hydrocarbyl of from 1 to about 20 carbons further containing heteroatoms of oxygen, sulfur, silicon; X is selected from the group consisting of an oxygen atom, a sulfur atom, an imine group substituted with a radical of R wherein R is selected from the group consisting of an alkyl with from 1 to about 6 carbon atoms, a phenyl, and a naphthyl; and wherein A is an aryl group containing from about 6 to about 30 carbon atoms.

7. An electroluminescent device in accordance with claim 6 wherein $R^1$, $R^2$ and $R^3$ are selected from the group consisting of hydrogen, fluorine, cyan, methyl, methoxyl; G is an alkyl with from about 1 to about 20 carbons, a phenyl; an alkylphenyl, an alkoxyphenyl; and A is selected from the group consisting of a phenyl, a tolyl, and a naphthyl.

8. An electroluminescent device in accordance with claim 6 wherein said heteroatom is oxygen.

9. An electroluminescent device in accordance with claim 6 wherein said heteroatom is sulfur.

10. An electroluminescent device in accordance with claim 6 wherein said heteroatom is silicon.

11. An electroluminescent device in accordance with claim 6 wherein said heteroatom is nitrogen.

12. An electroluminescent device in accordance with claim 1 wherein Ar is selected from the group consisting of a phenylene, a biphenyl-4,4'-diyl, a naphthalene, a stilben-4,4'-diyl, and a fluoren-2,7-diyl.

13. An electroluminescent device in accordance with claim 1 wherein said carbazole is Compound-1

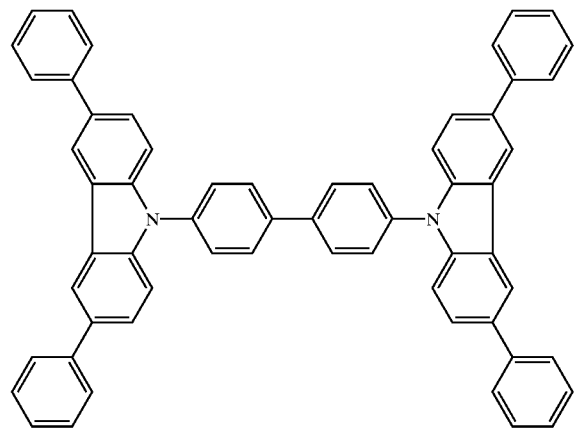

Compound-2

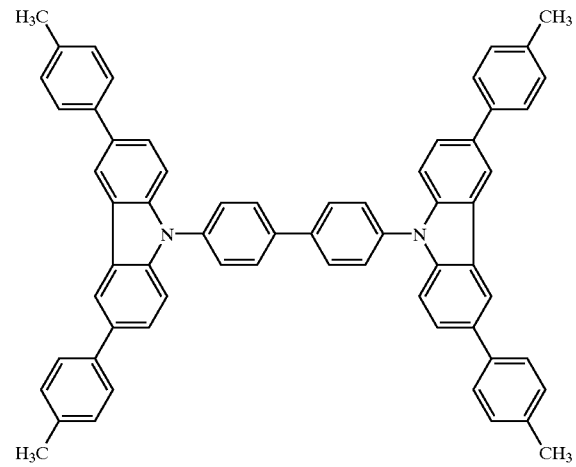

Compound-3

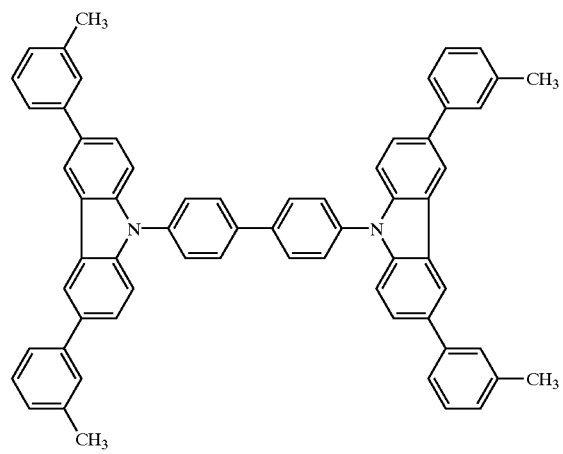

Compound-4

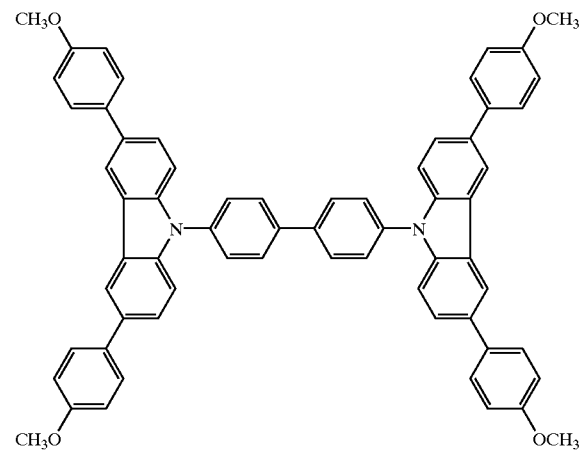

-continued
Compound-5
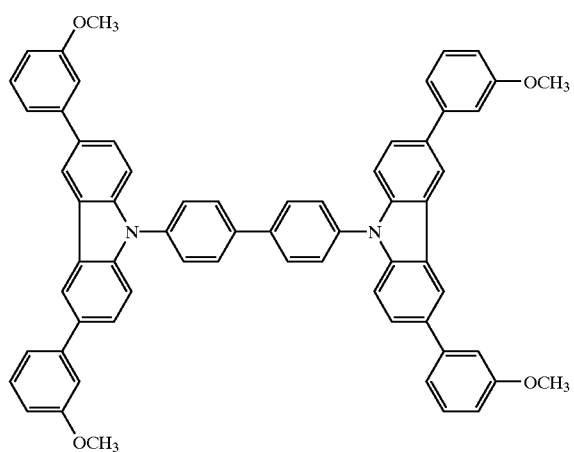
Compound-6
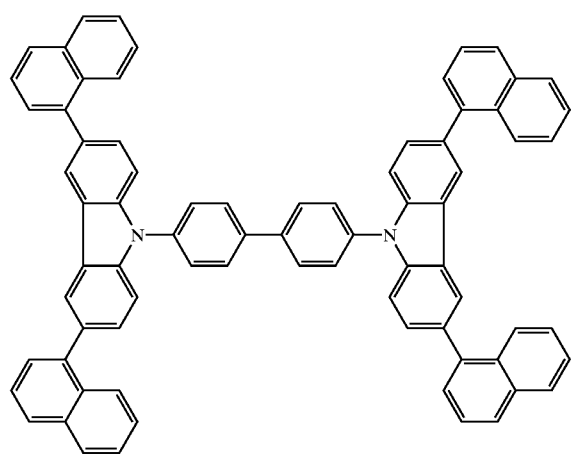
Compound-7
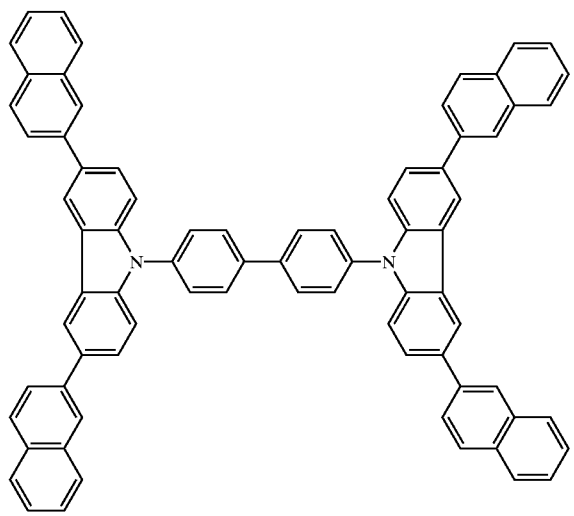
Compound-8
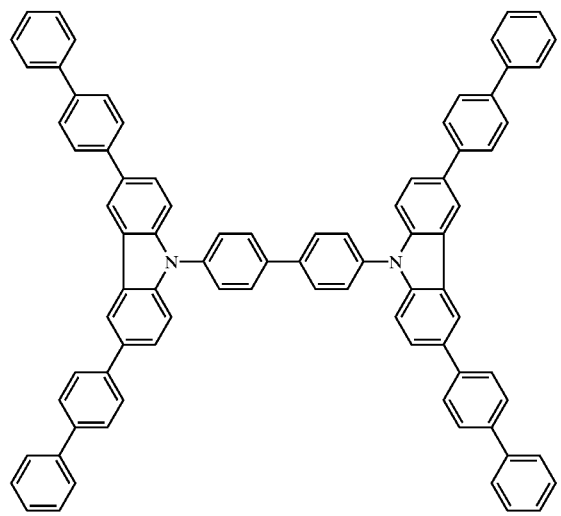
Compound-9
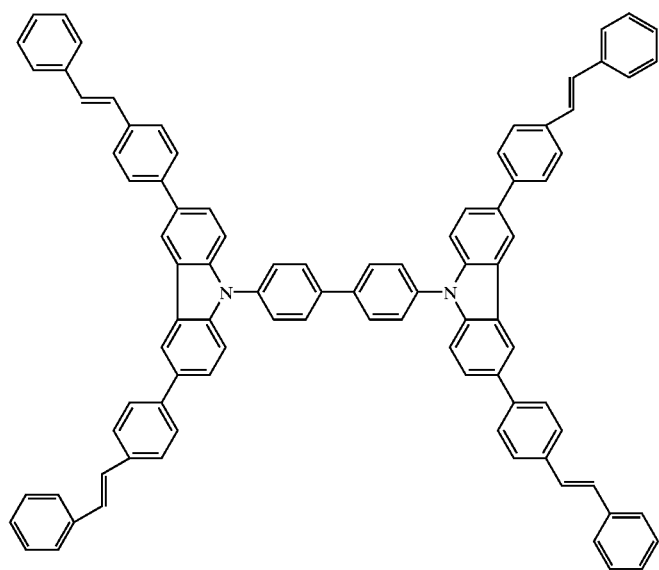

-continued

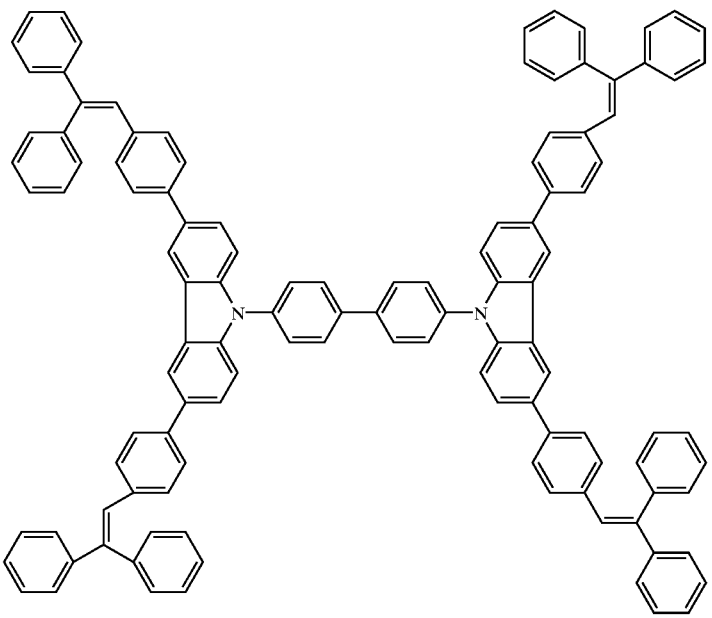

Compound-10

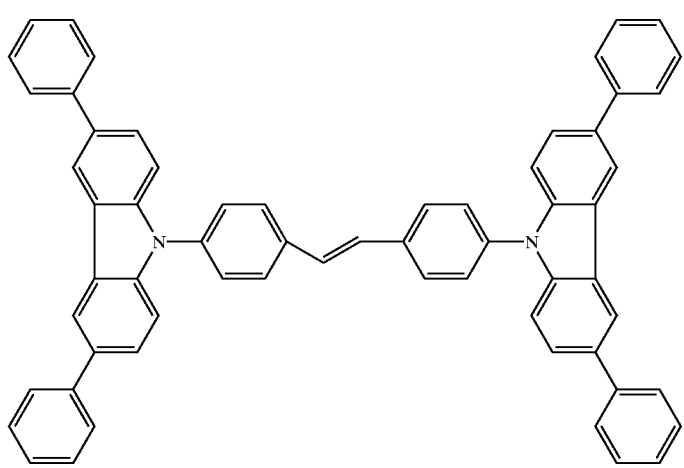

Compound-11

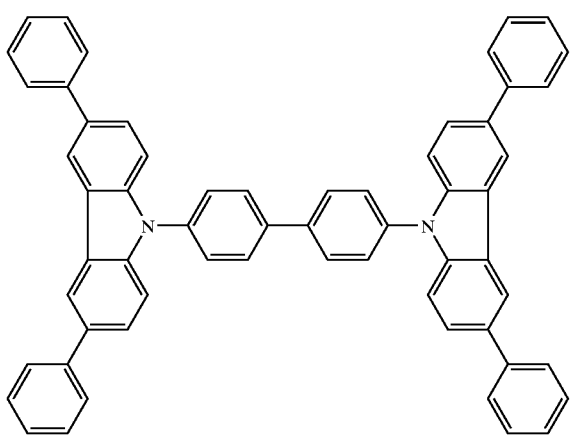

14. An electroluminescent device in accordance with claim 1 wherein said hydrocarbyl $R^1$, $R^2$, $R^3$, and $R^4$ contain from 1 to about 16 carbon atoms.

15. An electroluminescent device in accordance with claim 1 wherein said aryl contains from 6 to about 24 carbon atoms.

16. An electroluminescent device in accordance with claim 1 wherein said carbazole is a compound of the Formula 17. An electroluminescent device in accordance with claim 1 wherein said carbazole is a compound of the Formula

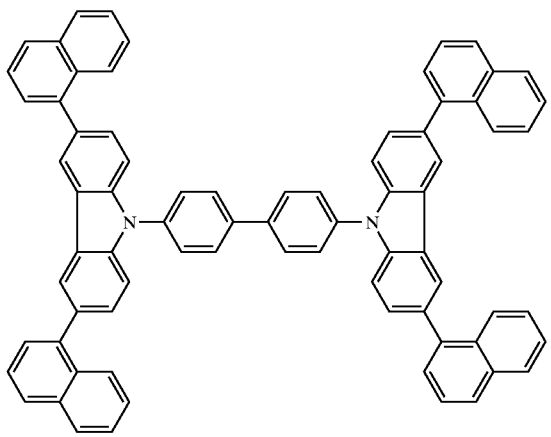

18. An electroluminescent device in accordance with claim 1 wherein said carbazole is a compound of the Formula

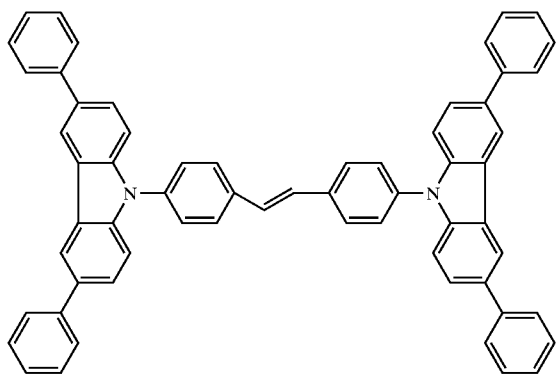

19. An electroluminescent device in accordance with claim 1 wherein each $R^1$, $R^2$, $R^3$ and $R^4$ is independently methyl.

20. An electroluminescent device in accordance with claim 1 wherein each $R^1$, $R^2$, $R^3$ and $R^4$ is hydrocarbyl.

21. An electroluminescent device in accordance with claim 1 wherein each $R^1$, $R^2$, $R^3$ and $R^4$ is a hydrocarbonyl containing a heteroatom.

22. An electroluminescent device in accordance with claim 1 wherein Ar is aryl.

23. An electroluminescent device in accordance with claim 1 wherein Ar is a heteroaromatic.

24. An electroluminescent device comprised of a first electrode, a second electrode, and an organic layer containing a carbazole compound illustrated by the formula

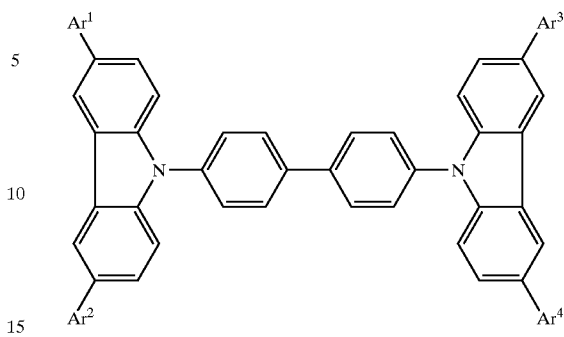

wherein $Ar^1$, $Ar^2$, $Ar^3$, and $Ar^4$ are each an aryl group with from about 6 to about 24 carbons.

25. An electroluminescent device in accordance with claim 24 wherein $Ar^1$, $Ar^2$, $Ar^3$, and $Ar^4$ are each independently an aryl selected from the group consisting of a phenyl, a stilbenyl, a biphenyl, a naphthyl, an anthyl group, a thienyl, a carbozolyl, and a quinolyl.

26. An electroluminescent device in accordance with claim 25 wherein said aryl contains a substituent selected from the group consisting of an alkyl group with from 1 to about 6 carbon atoms, an alkoxy group with from 1 to about 6 carbon atoms, a halogen, and a cyano group.

27. An electroluminescent device in accordance with claim 24 wherein $Ar^1$, $Ar^2$, $Ar^3$, and $Ar^4$ are each independently selected from the group consisting of phenyl, a tolyl, a xylyl, a methyoxyphenyl, a fluorophenyl, a stilbenyl, a biphenyl, a naphthyl, and an anthryl.

28. An electroluminescent device in accordance with claim 24 wherein said Ars are each a heteroaromatic substituent.

29. An electroluminescent device in accordance with claim 28 wherein said heteroatom of said aromatic is oxygen, sulfur, nitrogen, or silicon.

30. An electroluminescent device comprised in sequence of an anode, a hole transport layer, an electron transport layer, and a cathode, wherein said hole transport layer is comprised of a carbazole

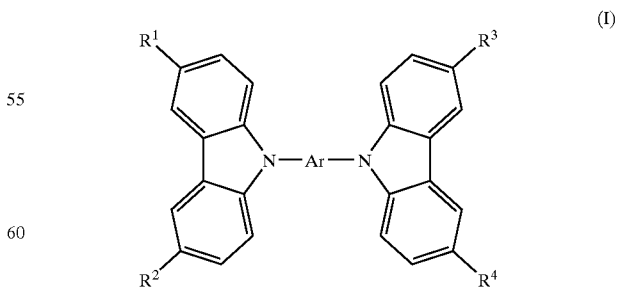

wherein $R^1$, $R^2$, $R^3$, and $R^4$ are independently selected from the group consisting of a hydrocarbyl, and wherein Ar is an aryl; and a

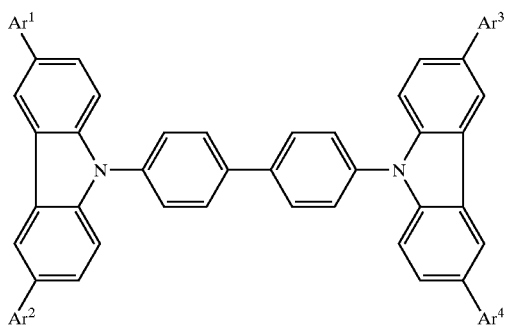

(II)

wherein $Ar^1$, $Ar^2$, $Ar^3$, and $Ar^4$ are each an aryl group with from about 6 to about 24 carbons.

31. An electroluminescent device in accordance with claim 30 wherein said electron transport layer is comprised of a metal chelate compound of an 8-hydroxyquinoline.

32. An electroluminescent device in accordance with claim 30 further containing a buffer layer, a hole injection assistant layer, said hole transport layer, said electron transport layer, said anode and said cathode.

33. An electroluminescent device in accordance with claim 32 wherein said buffer layer is comprised of copper phthalocyanine, and said hole injection assistant layer is a N,N,N',N'-tetraarylbenzidine.

34. An electroluminescent device in accordance with claim 30 wherein light emissions originate from the carbazole hole-transport layer, the electron transport layer, or both of said layers.

35. An electroluminescent device in accordance with claim 30 and further containing a light emitting layer.

36. An electroluminescent device in accordance with claim 35 wherein said light emitting layer is a fluorescent hydrocarbon compound with a light emission of from about 400 nanometers to about 680 nanometers.

37. A device comprised of a first electrode, a second electrode, and a carbazole of the formula

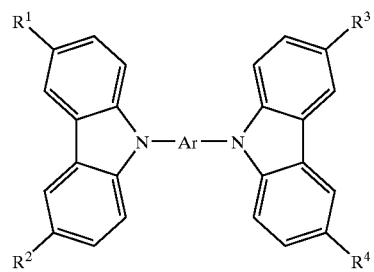

(I)

wherein $R^1$, $R^2$, $R^3$, and $R^4$ are independently selected from the group consisting of a hydrocarbyl, and wherein Ar is an aryl; and a hydrocarbyl containing a heteroatom of oxygen, sulfur, silicon, or nitrogen; or a heteroaromatic group containing a heteroatom of oxygen, sulfur, silicon, or nitrogen.

38. An electroluminescent device in accordance with claim 37 wherein said $R^1$, $R^2$, $R^3$, and $R^4$ are each independently alkoxy.

* * * * *